(12) United States Patent
Solomon et al.

(10) Patent No.: US 12,174,281 B2
(45) Date of Patent: Dec. 24, 2024

(54) SYSTEM AND METHOD FOR CONTROL OF MOTION IN MEDICAL IMAGES USING AGGREGATION

(71) Applicants: Regents of the University of Minnesota, Minneapolis, MN (US); Duke University, Durham, NC (US)

(72) Inventors: Oren Solomon, Minneapolis, MN (US); Noam Harel, Minneapolis, MN (US); Guillermo Sapiro, Durham, NC (US); Edward Auerbach, Minneapolis, MN (US); Steen Moeller, Minneapolis, MN (US); Remi Patriat, Minneapolis, MN (US); Henry Braun, Minneapolis, MN (US); Tara Palnitkar, Minneapolis, MN (US)

(73) Assignees: Regents of the University of Minnesota, Minneapolis, MN (US); Duke University, Durham, NC (US)

(*) Notice: Subject to any disclaimer, the term of this patent is extended or adjusted under 35 U.S.C. 154(b) by 172 days.

(21) Appl. No.: 17/947,761

(22) Filed: Sep. 19, 2022

(65) Prior Publication Data

US 2023/0136320 A1 May 4, 2023

Related U.S. Application Data

(60) Provisional application No. 63/249,176, filed on Sep. 28, 2021.

(51) Int. Cl.
*G01R 33/565* (2006.01)
*A61B 5/055* (2006.01)
*G01R 33/56* (2006.01)

(52) U.S. Cl.
CPC .......... *G01R 33/5608* (2013.01); *A61B 5/055* (2013.01); *G01R 33/56509* (2013.01); *G06T 2207/10088* (2013.01)

(58) Field of Classification Search
CPC .................................................. G01R 33/5608
See application file for complete search history.

(56) References Cited

U.S. PATENT DOCUMENTS

| 9,998,666 B2 | 6/2018 | Sapiro et al. |
| 2009/0232373 A1 | 9/2009 | Licato et al. |

(Continued)

OTHER PUBLICATIONS

Levin et al., Understanding and evaluating blind deconvolution algorithms, 2009 IEEE Conference on Computer Vision and Pattern Recognition, IEEE, 2009, pp. 1964-1971.

(Continued)

*Primary Examiner* — Alesa Allgood
(74) *Attorney, Agent, or Firm* — QUARLES & BRADY LLP

(57) ABSTRACT

A system and method are provided for creating magnetic resonance (MR) images with reduced motion artifacts from the MR data from which the images are produced. The method includes selecting a candidate image from a plurality of candidate images reconstructed from the MR data. The method also includes registering the candidate image to a reference image, comparing the candidate image to a consistency map, and, based on comparing the candidate image using the consistency map, selecting a blending algorithm. The method also includes generating a blended image using the blending algorithm and the candidate image and repeating these steps for each candidate image. The method also includes performing a Fourier aggregation to generate a combined image and displaying the combined image with reduced motion artifacts compared to the plurality of candidate images.

21 Claims, 15 Drawing Sheets

(56) References Cited

U.S. PATENT DOCUMENTS

| | | |
|---|---|---|
| 2010/0128841 A1 | 5/2010 | Imas et al. |
| 2011/0311115 A1 | 12/2011 | Li et al. |
| 2012/0189195 A1 | 7/2012 | Paik et al. |
| 2013/0051644 A1* | 2/2013 | Nett ..................... G06T 11/008 382/131 |
| 2015/0262341 A1 | 9/2015 | Nash et al. |
| 2016/0217577 A1 | 7/2016 | Tom et al. |
| 2016/0241884 A1 | 8/2016 | Messing |
| 2016/0330374 A1 | 11/2016 | Ilic et al. |
| 2017/0054909 A1 | 2/2017 | Iancu |
| 2017/0091550 A1 | 3/2017 | Feng et al. |
| 2017/0094164 A1 | 3/2017 | Shabtay et al. |
| 2017/0206671 A1 | 7/2017 | Pollard et al. |
| 2017/0236407 A1 | 8/2017 | Rhoads et al. |

OTHER PUBLICATIONS

Levin et al., Efficient marginal likelihood optimization in blind deconvolution, Computer Science and Artificial Intelligence Laboratory Technical Report, 2011, pp. 1-12.

Lim et al., Clinical applications of 3D T2-weighted MRI in pelvic imaging, Abdominal Imaging, 2014, 39:1052-1062.

Loktyushin et al., Blind retrospective motion correction of MR images, Magnetic Resonance in Medicine, 2013, 70 (6): 1608-1618.

Loktyushin et al., Blind multirigid retrospective motion correction of MR images, Magnetic Resonance in Medicine, 2015, 73(4): 1457-1468.

Loktyushin et al., Retrospective motion correction of magnitude-input MR images, in "Machine Learning Meets Medical Imaging," First International Workshop, MLMMI 2015, Held in Conjunction with ICML 2015, Revised Selected Papers 1, Springer International Publishing, 2015, pp. 3-12.

Lowe, Object recognition from local scale-invariant features, Proceedings of the Seventh IEEE International Conference on Computer Vision, IEEE, 1999, 2:1-8.

Lowe, Distinctive image features from scale-invariant keypoints, International Journal of Computer Vision, 2004, 60:91-110.

Lustig et al., Compressed sensing Mri, IEEE Signal Processing Magazine, 2008, 25(2):72-82.

Maclaren et al., Prospective motion correction in brain imaging: a review, Magnetic Resonance in Medicine, 2013, 69(3):621-636.

Madore et al., A new way of averaging with applications to MRI, Medical Physics, 1996, 23(1): 109-113.

Moisan et al., Automatic homographic registration of a pair of images, with a contrario elimination of outliers, Image Processing On Line, 2012, 2:56-73.

Mok et al., Large deformation diffeomorphic image registration with laplacian pyramid networks, arXiv preprint arxiv:2006.16148, 2020, 11 pages.

Morelli et al., An image-based approach to understanding the physics of MR artifacts, Radiographics, 2011, 31 (3):849-866.

Nowacki et al., Targeting accuracy of the subthalamic nucleus in deep brain stimulation surgery: comparison between 3 T T2-weighted magnetic resonance imaging and microelectrode recording results, Operative Neurosurgery, 2018, 15(1):66-71.

Odille et al., Generalized reconstruction by inversion of coupled systems (GRICS) applied to free-breathing MRI, Magnetic Resonance in Medicine: An Official Journal of the International Society for Magnetic Resonance in Medicine, 2008, 60(1): 146-157.

Park et al., Gyro-based multi-image deconvolution for removing handshake blur, Proceedings of the IEEE Conference on Computer Vision and Pattern Recognition, 2014, 8 pages.

Patriat et al., Individualized tractography-based parcellation of the globus pallidus pars interna using 7T Mri in movement disorder patients prior to DBS surgery, Neuroimage, 2018, 178: 198-209.

Pawar et al., Motion correction in MRI using deep convolutional neural network, Proceedings of the ISMRM Scientific Meeting & Exhibition, 2018, 26: 1174, 2 pages.

Pipe, Motion correction with Propeller Mri: application to head motion and free-breathing cardiac imaging, Magnetic Resonance in Medicine: An Official Journal of the International Society for Magnetic Resonance in Medicine, 1999, 42(5): 963-969.

Polak et al., Scout accelerated motion estimation and reduction, Magnetic Resonance in Medicine, 2022, 87(1): 163-178.

Pruessmann et al., Advances in sensitivity encoding with arbitrary k-space trajectories, Magnetic Resonance in Medicine: An Official Journal of the International Society for Magnetic Resonance in Medicine, 2001, 46(4):638-651.

Qin et al., Prospective head-movement correction for high-resolution MRI using an in-bore optical tracking system, Magnetic Resonance in Medicine: An Official Journal of the International Society for Magnetic Resonance in Medicine, 2009, 62(4): 924-934.

Rav-Acha et al., Two motion-blurred images are better than one, Pattern Recognition Letters, 2005, 26(3):311-317.

Regini et al., Rectal tumour volume (GTV) delineation using T2-weighted and diffusion-weighted MRI: Implications for radiotherapy planning, European Journal of Radiology, 2014, 83(5):768-772.

Sánchez et al., TV-L1 optical flow estimation, Image Processing On Line, 2013, 3:137-150.

Siemens Healthineersusa , Pediatric Protocols, Retrieved from https://www.siemens-healthineers.com/en-us/magnetic-resonance-imaging/magnetom-world/clinical-corner/protocols/pediatric-protocols, Version Accessed on Jul. 9, 2024, 8 pages.

Soellinger et al., 3D cine displacement-encoded MRI of pulsatile brain motion, Magnetic Resonance in Medicine: An Official Journal of the International Society for Magnetic Resonance in Medicine, 2009, 61(1): 153-162.

Solomon et al., Deep-learning based fully automatic segmentation of the globus pallidus interna and externa using ultra-high 7 Tesla MRI, Human Brain Mapping, 2021, 42(9):2862-2879.

Sroubek et al., Robust multichannel blind deconvolution via fast alternating minimization, IEEE Transactions on Image Processing, 2012, 21(4): 1687-1700.

Stark et al., Detection of hepatic metastases: analysis of pulse sequence performance in MR imaging, Radiology, 1986, 159(2):365-370.

Stark et al., Motion artifact reduction with fast spin-echo imaging, Radiology, 1987, 164(1): 183-191.

Tanitame et al., Clinical utility of optimized three-dimensional T1-, T2-, and T2 *-weighted sequences in spinal magnetic resonance imaging, Japanese Journal of Radiology, 2017, 35(4): 135-144.

Teeuwisse et al., Quantitative assessment of the effects of high-permittivity pads in 7 Tesla MRI of the brain, Magnetic Resonance in Medicine, 2012, 67(5):1285-1293.

Terem et al., 3D amplified MRI (aMRI), Magnetic Resonance in Medicine, 2021, 86(3): 1674-1686.

Tsuboyama et al., Comparison of HASTE with multiple signal averaging versus conventional turbo spin echo sequence: a new option for T2-weighted MRI of the female pelvis, European Radiology, 2020, 30:3245-3253.

Universitats Klinikum Freiburg, Department of Radiology—Medical Physics, PMC Core Research, Retrieved from https://www.uniklinik-freiburg.de/mr-en/research-groups/mr-technologies/motion-correction/core-research.html, Version Accessed on Jul. 9, 2024, 2 pages.

Usman et al., Motion corrected compressed sensing for free-breathing dynamic cardiac MRI, Magnetic Resonance in Medicine, 2013, 70(2):504-516.

Usman et al., Retrospective motion correction in multishot MRI using generative adversarial network, Scientific Reports, 2020, 10(1):4786, pp. 1-11.

Van Der Kouwe et al., Real-time rigid body motion correction and shimming using cloverleaf navigators, Magnetic Resonance in Medicine: An Official Journal of the International Society for Magnetic Resonance in Medicine, 2006, 56 (5): 1019-1032.

Vasques et al., Cerebral magnetic resonance imaging feasibility in patients with implanted neurostimulation system for deep brain stimulation, The Open Magnetic Resonance Journal, 2008, 1(1): 1-8.

(56) References Cited

OTHER PUBLICATIONS

Mtek et al., Randomized trial of pallidotomy versus medical therapy for Parkinson's disease, Annals of Neurology: Official Journal of the American Neurological Association and the Child Neurology Society, 2003, 53(5): 558-569.

Wang et al., Image quality assessment: from error visibility to structural similarity, IEEE Transactions on Image Processing, 2004, 13(4): 1-14.

Welch et al., Spherical navigator echoes for full 3D rigid body motion measurement in MRI, Magnetic Resonance in Medicine: An Official Journal of the International Society for Magnetic Resonance in Medicine, 2002, 47(1):32-41.

White et al., PROMO: real-time prospective motion correction in MRI using image-based tracking, Magnetic Resonance in Medicine: An Official Journal of the International Society for Magnetic Resonance in Medicine, 2010, 63 (1):91-105.

Whyte et al., Non-uniform deblurring for shaken images, International Journal of Computer Vision, 2012, 98 (2): 168-186.

Wong et al., A strategy for sampling on a sphere applied to 3D selective RF pulse design, Magnetic Resonance in Medicine, 1994, 32(6):778-784.

Xiao, Camera-motion and effective spatial resolution, International Congress of Imaging Science: Final Program and Proceedings, Society for Science and Technology, 2006, pp. 33-36.

Yamakazi et al., Visualization of brain white matter tracts using heavily t2-weighted three-dimensional fluid- attenuated inversion-recovery magnetic resonance imaging, Nagoya Journal of Medical Science, 2014, 76 (3-4):285-291.

Yang et al., Sparse MRI for motion correction, arXiv preprint arXiv:1302.0077, 2013, 4 pages.

Yuan et al., Blurred/non-blurred image alignment using sparseness prior, 2007 IEEE 11th International Conference on Computer Vision, IEEE, 2007, 8 pages.

Zach et al., A duality based approach for realtime tv-L1 optical flow, Pattern Recognition: 29th DAGM Symposium, Proceedings 29, Springer-Verlag Berlin Heidelberg, 2007, pp. 214-223.

Zaitsev et al., Magnetic resonance imaging of freely moving objects: prospective real-time motion correction using an external optical motion tracking system, Neuroimage, 2006, 31(3): 1038-1050.

Zaitsev et al., Motion artifacts in Mri: A complex problem with many partial solutions, Journal of Magnetic Resonance Imaging, 2015, 42(4): 887-901.

Zhang et al., Gradient-directed composition of multi-exposure images, 2010 IEEE Computer Society Conference on Computer Vision and Pattern Recognition, IEEE, 2010, pp. 530-536.

Zhang et al., Multi-image blind deblurring using a coupled adaptive sparse prior, Proceedings of the IEEE Conference on Computer Vision and Pattern Recognition, 2013, pp. 1051-1058.

Zhu et al., Deconvolving PSFs for a better motion deblurring using multiple images, Computer Vision—ECCV 2012: 12th European Conference on Computer Vision, Proceedings, Part V 12, Springer-Verlag Berlin Heidelberg, 2012, pp. 636-647.

Zitova et al., Image registration methods: a survey, Image and Vision Computing, 2003, 21(11): 977-1000.

Abosch et al., An assessment of current brain targets for deep brain stimulation surgery with susceptibility-weighted imaging at 7 tesla, Neurosurgery, 2010, 67(6): 1745-1756.

Ashburner, A fast diffeomorphic image registration algorithm, Neuroimage, 2007, 38(1): 95-113.

Atkinson et al., An autofocus algorithm for the automatic correction of motion artifacts in MR images, Biennial International Conference on Informational Processing in Medical Imaging, Springer Berlin Heidelberg, 1997, pp. 341-354.

Atkinson et al., Automatic correction of motion artifacts in magnetic resonance images using an entropy focus criterion, IEEE Transaction on Medical Imaging, 1997, 16(6):903-910.

Avants et al., Symmetric diffeomorphic image registration with cross-correlation: evaluating automated labeling of elderly and neurodegenerative brain, Medical Image Analysis, 2008, 12(1):26-41.

Barron et al., Systems and Experiment: Performance of optical flow techniques, International Journal of Computer Vision, 1994, 12(1):43-77.

Batchelor et al., Matrix description of general motion correction applied to multishot images, Magnetic Resonance in Medicine: An Official Journal of the International Society for Magnetic Resonance in Medicine, 2005, 54 (5):1273-1280.

Bilgic et al., Wave-CAIPI for highly accelerated 3D imaging, Magnetic Resonance in Medicine, 2015, 73 (6):2152-2162.

Boracchi et al., Modeling the performance of image restoration from motion blur, IEEE Transactions on Image Processing, 2012, 21(8):3502-3517.

Buades et al., A note on multi-image denoising, 2009 International Workshop on Local and Non-Local Approximation in Image Processing, IEEE, 2009, pp. 1-15.

Bydder et al., Detection and elimination of motion artifacts by regeneration of k-space, Magnetic Resonance in Medicine: An Official Journal of the International Society for Magnetic Resonance in Medicine, 2002, 47(4): 677-686.

Cai et al., Blind motion deblurring using multiple images, Journal of Computational Physics, 2009, 228(14):5057-5071.

Carignan et al., Quantifying the importance of high frequency components on the amplitude of physiological tremor, Experimental Brain Research, 2010, 202:299-306.

Chen et al., Robust dual motion deblurring, 2008 IEEE Conference on Computer Vision and Pattern Recognition, 2008, pp. 1-8.

Cho et al., Fast motion deblurring, ACM Transactions on Graphics, 2009, 28(5): 145, pp. 1-8.

Cho et al., Video deblurring for hand-held cameras using patch-based synthesis, ACM Transactions on Graphics, 2012, 31(4): 1-9.

Colom et al., Analysis and extension of the Ponomarenko et al. method, estimating a noise curve from a single image, Image Processing On Line, 2013, 3:173-197.

Cordero-Grande et al., Three-dimensional motion corrected sensitivity encoding reconstruction for multi-shot multi-slice MRI: application to neonatal brain imaging, Magnetic Resonance in Imaging, 2018, 79(3): 1365-1376.

Cordero-Grande et al., Motion-corrected MRI with DISORDER: distributed and incoherent sample orders for reconstruction deblurring using encoding redundancy, Magnetic Resonance in Medicine, 2020, 84(2):713-726.

Delbracio et al., The non-parametric sub-pixel local point spread function estimation is a well posed problem, International Journal of Computer Vision, 2012, 96: 175-194.

Delbracio et al., Burst deblurring: Removing camera shake through fourier burst accumulation, Proceedings of the IEEE Conference on Computer Vision and Pattern Recognition, 2015, pp. 2385-2393.

Delbracio et al., Hand-held video deblurring via efficient fourier aggregation, arXiv preprint arXiv:1509.05251, 2015, 14 pages.

Delbracio et al., Removing camera shake via weighted fourier burst accumulation, arXiv preprint arXiv: 1505.02731, 2015, 15 pages.

Dold et al., Prospective head motion compensation for MRI by updating the gradients and radio frequency during data acquisition, Medical Image Computing and Computer-Assisted Intervention—MICCAI 2005: 8th International Conference, Proceedings, Part I 8, Springer Berlin Heidelberg, 2005, pp. 482-489.

Duchin et al., Patient-specific anatomical model for deep brain stimulation based on 7 Tesla MRI, PloS One, 2018, 13(8): e0201469, pp. 1-23.

Duffy et al., Retrospective correction of motion artifact affected structural MRI images using deep learning of simulated motion, 1st Conference on Medical Imaging with Deep Learning, Amsterdam, The Netherlands, 2018, pp. 1-8.

Duffy et al., Retrospective motion artifact correction of structural MRI images using deep learning improves the quality of cortical surface reconstructions, Neuroimage, 2021, 230:117756, pp. 1-13.

Fergus et al., Removing camera shake from a single photograph, ACM Transactions on Graphics, 2006, 25 (3):787-794.

Fischler et al., Random sample consensus: a paradigm for model fitting with applications to image analysis and automated cartography, Communications of the ACM, 1981, 24(6):381-395.

(56) References Cited

OTHER PUBLICATIONS

Garrel et al., A highly efficient lucky imaging algorithm: Image synthesis based on Fourier amplitude selection, Publications of the Astronomical Society of the Pacific, 2012, 124(918): 861-867.
Gavant et al., A physiological camera shake model for image stabilization systems, Sensors, IEEE, 2011, 5 pages.
Ghafoorian et al., Transfer learning for domain adaptation in mri: Application in brain lesion segmentation, arXiv preprint arXiv: 1702.07841, 2017, 8 pages.
Ginat et al., 3 Tesla intraoperative MRI for brain tumor surgery, Journal of Magnetic Resonance Imaging, 2014, 39 (6): 1357-1365.
Godenschweger et al., Motion correction in MRI of the brain, Physics in Medicine & Biology, 2016, 61(5): R32-R56.
Gottliebson et al., 217 Normal human ventricular vol. and mass values in children ages 5-10 years using steady state free precession MRI, Journal of Cardiovascular Magnetic Resonance, 2008, 10(Suppl. 1):A78, pp. 1-2.
Griswold et al., Generalized autocalibrating partially parallel acquisitions (GRAPPA), Magnetic Resonance in Medicine: An Official Journal of the International Society for Magnetic Resonance in Medicine, 2002, 47(6): 1202-1210.
Han et al., k-space deep learning for accelerated MRI, arXiv preprint arXiv: 1805.03779, 2019, 16 pages.
Haro et al., Photographing paintings by image fusion, SIAM Journal on Imaging Sciences, 2012, 5(3): 1055-1087.
Holdsworth et al., Fast susceptibility-weighted imaging with three-dimensional short-axis propeller (SAP)-echo- planar imaging, Journal of Magnetic Resonance Imaging, 2015, 41(5): 1447-1453.
Hosseini et al., Dense recurrent neural networks for accelerated MRI: History-cognizant unrolling of optimization algorithms, IEEE Journal of Selected Topics in Signal Processing, 2020, 14(6): 1280-1291.
Ito et al., Blurburst: Removing blur due to camera shake using multiple images, ACM Transactions on Graphics, 2014, 3(1): 1-15.
Joshi et al., Seeing Mt. Rainier: Lucky imaging for multi-image denoising, sharpening, and haze removal, 2010 IEEE International Conference on Computational Photography, 2010, 8 pages.
Kim et al., Generalized video deblurring for dynamic scenes, Proceedings of the IEEE Conference on Computer Vision and Pattern Recognition, 2015, pp. 5426-5434.
Klawans, Individual manifestations of Parkinson's disease after ten or more years of levodopa, Movement Disorders: Official Journal of the Movement Disorder Society, 1986, 1(3): 187-192.
Klein et al., In vivo middle cerebral artery plaque imaging by high-resolution MRI, Neurology, 2006, 67(2):327-329.
Krishnan et al., Blind deconvolution using a normalized sparsity measure, CVPR 2011, IEEE, 2011, pp. 233-240.
Krüger et al., Combination of CT angiography and MRI in surgical planning of deep brain stimulation, Neuroradiology, 2018, 60:1151-1158.
Kundur et al., Blind image deconvolution, IEEE Signal Processing Magazine, 1996, 13(3):43-64.
Lebrun et al., Implementation of the "Non-Local Bayes" (NL-Bayes) Image Denoising Algorithm, Image Processing On Line, 2013, 3:1-42.
Lee et al., Improved abdominal MRI in non-breath-holding children using a radial k-space sampling technique, Pediatric Radiology, 2015, 45:840-846.

\* cited by examiner

SYSTEM AND METHOD FOR CONTROL OF MOTION IN MEDICAL IMAGES USING AGGREGATION

CROSS-REFERENCE TO RELATED APPLICATIONS

This application is based on, claims priority to, and incorporates herein by reference, U.S. Provisional Application Ser. No. 63/249,176, filed Sep. 28, 2021, and entitled, "SYSTEM AND METHOD FOR CONTROL OF MOTION IN MEDICAL IMAGES USING AGGREGATION."

STATEMENT REGARDING FEDERALLY SPONSORED RESEARCH

N/A

BACKGROUND

The present disclosure relates generally to systems and methods for magnetic resonance imaging ("MRI"). More particularly, the present disclosure relates to systems and methods for controlling against artifacts or clinically-unusable images caused by patient motion during MRI acquisitions.

When a substance, such as human tissue, is subjected to a uniform magnetic field (polarizing field $B_0$), the individual magnetic moments of the nuclei in the tissue attempt to align with this polarizing field, but precess about it in random order at their characteristic Larmor frequency. If the substance, or tissue, is subjected to a magnetic field (excitation field $B_1$) that is in the x-y plane and that is near the Larmor frequency, the net aligned moment, $M_z$, may be rotated, or "tipped", into the x-y plane to produce a net transverse magnetic moment $M_{xy}$. A signal is emitted by the excited nuclei or "spins", after the excitation signal $B_1$ is terminated, and this signal may be received and processed to form an image.

When utilizing these "MR" signals to produce images, magnetic field gradients ($G_x$, $G_y$, and $G_z$) are employed. Typically, the region to be imaged is scanned by a sequence of measurement cycles in which these gradients vary according to the particular localization method being used. The resulting set of received MR signals are digitized and processed to reconstruct the image using one of many well-known reconstruction techniques.

Despite decades of significant advances, MRI has long acquisition times relative to other imaging modalities, such as x-ray. To acquire a high quality MR image, the subject is required to lie still for the entire duration of the scan. Generally, an MR imaging process is composed of several scans, and each scan can span several to tens of minutes. Many patients, including, patients with various motor dysfunctions such as Parkinson's disease (PD), essential tremor (ET), and dystonia, cannot lie still during each of the individual scans, even while on medications. Thus, it is not uncommon for MR images to include artifacts or otherwise be compromised by motion. Often, repeating a scan or an entire imaging session may be required, which adds additional discomfort to patients who are already struggling to remain still and that may still not be successful. Furthermore, each repetition further increases costs. Thus, it is common for clinical images to be at least partially degraded by motion. Reliance on motion corrupted images may lead to impaired diagnosis or sub-optimal surgery planning.

Achieving motion robust images is a "shutter-speed" challenge in MRI. For example, navigator-based techniques change the pulse sequence during acquisition to account for motion. Motion estimation is typically achieved by performing low-resolution navigator acquisitions between the actual data acquisition. Many techniques rely on intricate k-space trajectories for prospective motion correction, such has a circular navigator that is acquired in three orthogonal planes for prospective rigid-body motion correction, spherical navigators, or more elaborate k-space trajectories. However, all k-space based navigators require accurate and consistent k-space sampling trajectories between repetitions, such that rigid body movement parameters can be estimated. This assumption can be violated by several factors, including gradient instabilities and magnetic field inhomogeneities. Moreover, some techniques require multiple acquisitions for 3D movement estimation and are adversely affected by out-of-plane motion or insufficiently dense k-space sampling.

Even in acquisitions with fast recovery rates, such as T2-weighted acquisitions, this prospective motion correction may require additional acquisition time, which only exacerbates the fundamental problem of the imaging process taking too long for the patient to remain still.

In addition, all these techniques strictly rely on the assumption of rigid-body movement. In many cases this assumption holds, but not in all cases. For example, when neck and jaw movement occurs during the acquisition, assumptions of rigid-body movement fails. Similarly, respiratory or cardiac motion in the abdomen does not result in rigid-body movement.

Camera-based motion-correction techniques have also been suggested. However, these systems require additional external and often expensive hardware to be placed within the bore of the magnet. This complicates session setup and requires repeated calibration.

Recently, deep-learning based frameworks have also been suggested for the removal of motion artifacts from MR acquisitions. These techniques rely on supervised training of an encoder-decoder architecture on MR acquisitions with motion artifacts. Although such data-driven approaches do not require additional hardware or changes of the MR pulse sequence, they require actual knowledge of the motion mechanics to make viable training tools. As a result, such systems have reported success in correcting mild to moderate motion corrupted cases, but often fail when the motion is too severe and/or complex. Moreover, the network can be thought of as learning a prior for replacing voxels with motion artifacts with sharp and clean voxels. This approach may introduce erroneous synthetic data.

Motion reduction approaches which exploit sparsity of the acquired k-space data in some transform domain have also been suggested. However, these approaches have been applied to rigid translations and rely on explicit modelling of the motion degradation mechanism; namely, strictly rigid-body motion. Thus, deformation or other non-rigid motion, including complex motion, still yields substantially motion-corrupted images using these systems.

Thus, there is a need for systems and methods to overcome the drawbacks with traditional systems for controlling or correcting motion in MRI data and the resulting images.

SUMMARY

The present disclosure overcomes the aforementioned drawbacks by providing systems and methods for controlling against or mitigating motion artifacts, as well as image blur and noise in MRI standard clinical acquisitions. The systems and methods provided herein, which may be referred to as motion robust magnetic resonance imaging (MOTOR-MRI), do not require changes to the acquisition protocols, do not rely on any assumption of type of movement (e.g., rigid body movement), and do not require explicit knowledge of the blurring/motion mechanism. Rather, multiple scan repetitions (e.g., repeated individual scans (RIS)), which may occur within the same acquisition session, can be used to create blended images that are free of or have reduced instances of motion. In accordance with the systems and methods provided herein, the acquisition process can be broken down into several individual sessions or repetitions that improve the signal-to-noise ratio (SNR) of the final image, compared, for example, with a single acquired repetition. The individual repetitions can be selectively combined or blended together to produce a final dataset that is motion robust. MOTOR-MRI can operate directly on images reconstructed from each scan repetition, and as such can be used as a stand-alone motion reduction solution or it can complement other motion correction techniques (regardless of k-space acquisition schemes).

In accordance with one aspect of the disclosure, a method is provided that includes (a) accessing a plurality of candidate images reconstructed from MR data acquired with multiple repetitions of region of interest (ROI) in a subject, wherein at least a portion of the plurality of candidate images includes motion artifacts. The method also includes (b) selecting a candidate image of the ROI in the subject, (c) registering the candidate image to a reference image, and (d) comparing the candidate image to a consistency map. The method further includes (e), based on comparing the candidate image using the consistency map, selecting a blending algorithm and (f) generating a blended image using the blending algorithm and the candidate image. The method then includes (g) repeating steps (b)-(f) for each candidate image and (h) performing a Fourier aggregation to generate a combined image. The method also includes (i) displaying the combined image with reduced motion artifacts compared to the plurality of candidate images.

In accordance with another aspect of the disclosure, a magnetic resonance imaging (MRI) system is provided that includes a magnet system configured to generate a polarizing magnetic field about at least a portion of a subject arranged in the MRI system, a plurality of gradient coils configured to apply magnetic gradients to the polarizing magnetic field, and a radio frequency (RF) system configured to apply an excitation field to the subject and acquire MR image data from the subject. The MRI system also includes a computer system programmed to carry out steps comprising (a) controlling the plurality of gradient coils and the RF system to acquire MR data as multiple repetitions of region of interest (ROI) in the subject, (b) reconstructing a plurality of candidate images from the MR data, wherein at least a portion of the plurality of candidate images includes motion artifacts, and (c) selecting a candidate image of the ROI in the subject. The computer system is further programmed to carry out steps including (d) registering the candidate image to a reference image, (e) analyzing the candidate image using a consistency map, and (f), based on analyzing the candidate image using the consistency map, select a blending algorithm. The computer system is also programmed to carry out steps including (g) generating a blended image using the blending algorithm and the candidate image, (h) repeating steps (c)-(g) for each candidate image reconstructed from the MR image data in step (b), and (i) performing a Fourier aggregation to generate a combined image. The MRI system also includes a display to display the combined image with reduced motion artifacts compared to the plurality of candidate images The foregoing and other aspects and advantages of the invention will appear from the following description. In the description, reference is made to the accompanying drawings, which form a part hereof, and in which there is shown by way of illustration a preferred embodiment of the invention. Such embodiment does not necessarily represent the full scope of the invention, however, and reference is made therefore to the claims and herein for interpreting the scope of the invention.

DETAILED DESCRIPTION

Figure 1:
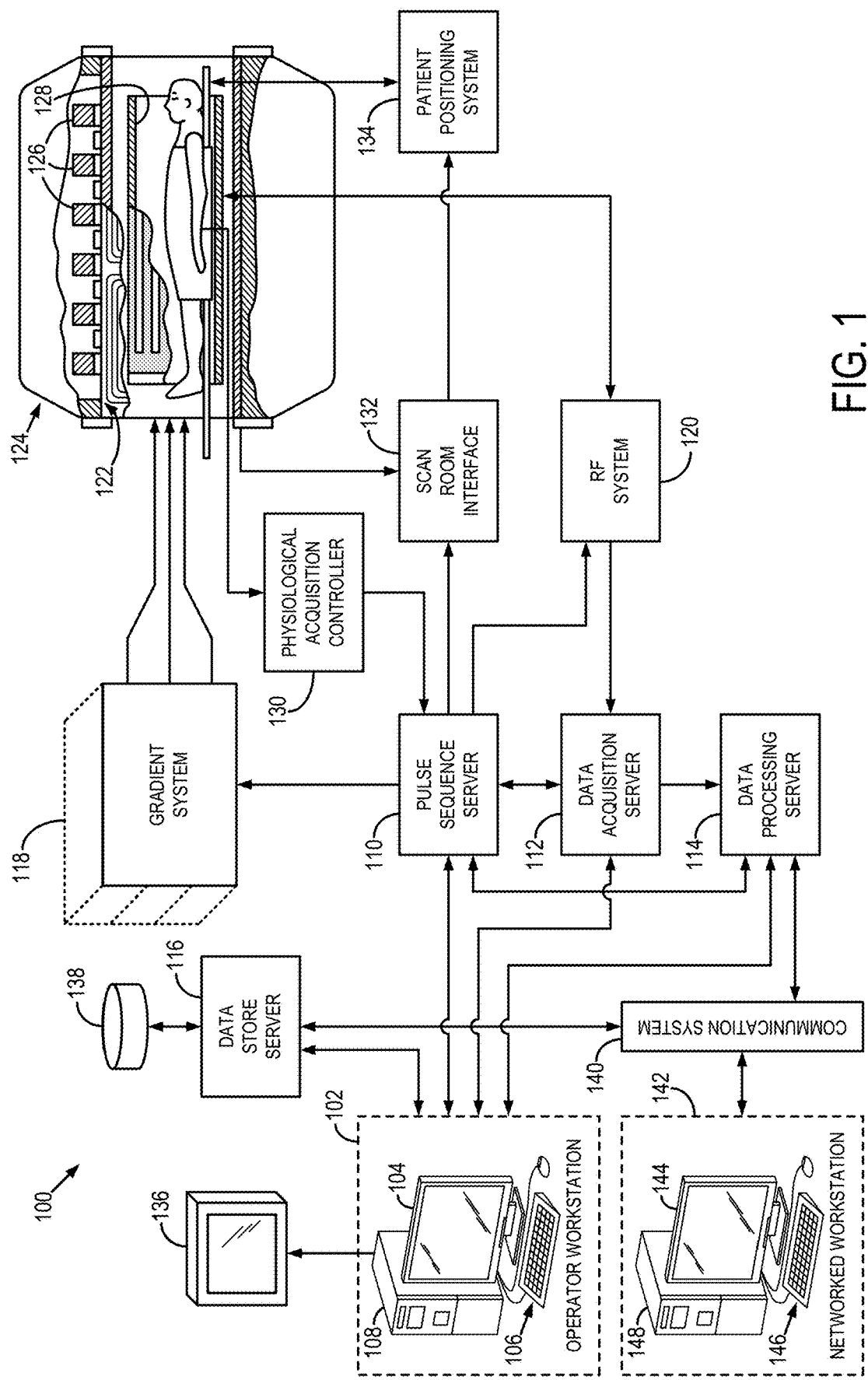
FIG. 1 is a block diagram of an exemplary magnetic resonance imaging ("MRI") system configured in accordance with the present disclosure.

Referring now to FIG. 1, a magnetic resonance imaging (MRI) system 100 is provided that may be configured, programmed, or otherwise utilized in accordance with the present disclosure. The MRI system 100 includes an operator workstation 102, which will typically include a display 104, one or more input devices 106 (such as a keyboard and mouse or the like), and a processor 108. The processor 108 may include a commercially available programmable machine running a commercially available operating system. The operator workstation 102 provides the operator interface that enables scan prescriptions to be entered into the MRI system 100. In general, the operator workstation 102 may be coupled to multiple servers, including a pulse sequence server 110; a data acquisition server 112; a data processing server 114; and a data store server 116. The operator workstation 102 and each server 110, 112, 114, and 116 are connected to communicate with each other. For example, the servers 110, 112, 114, and 116 may be connected via a communication system 140, which may include any suitable network connection, whether wired, wireless, or a combination of both. As an example, the communication system 140 may include both proprietary or dedicated networks, as well as open networks, such as the internet.

The pulse sequence server 110 functions in response to instructions downloaded from the operator workstation 102 to operate a gradient system 118 and a radiofrequency (RF) system 120. Gradient waveforms to perform the prescribed scan are produced and applied to the gradient system 118, which excites gradient coils in an assembly 122 to produce the magnetic field gradients $G_x$, $G_y$, $G_z$ used for position encoding magnetic resonance signals. The gradient coil assembly 122 forms part of a magnet assembly 124 that includes a polarizing magnet 126 and a whole-body RF coil 128 (as well as local coils, such as head coils).

RF waveforms are applied by the RF system 120 to the RF coil 128, or a separate local coil (not shown in FIG. 1), in order to perform the prescribed magnetic resonance pulse sequence. Responsive magnetic resonance signals detected by the RF coil 128, or a separate local coil, are received by the RF system 120, where they are amplified, demodulated, filtered, and digitized under direction of commands produced by the pulse sequence server 110. The RF system 120 includes an RF transmitter for producing a wide variety of RF pulses used in MRI pulse sequences. The RF transmitter is responsive to the scan prescription and direction from the pulse sequence server 110 to produce RF pulses of the desired frequency, phase, and pulse amplitude waveform. The generated RF pulses may be applied to the whole-body RF coil 128 or to one or more local coils or coil arrays.

The RF system 120 also includes one or more RF receiver channels. Each RF receiver channel includes an RF preamplifier that amplifies the magnetic resonance signal received by the coil 128 to which it is connected, and a detector that detects and digitizes the I and Q quadrature components of the received magnetic resonance signal. The magnitude of the received magnetic resonance signal may, therefore, be determined at any sampled point by the square root of the sum of the squares of the I and Q components (i.e., M= $\sqrt{I^2+Q^2}$) and the phase of the received magnetic resonance signal may also be determined according as the inverse tangent of the Q component over the I component (i.e., $\phi=\tan^{-1}(Q/I)$).

The pulse sequence server 110 also optionally receives patient data from a physiological acquisition controller 130. By way of example, the physiological acquisition controller 130 may receive signals from a number of different sensors connected to the patient, such as electrocardiograph (ECG) signals from electrodes, or respiratory signals from a respiratory bellows or other respiratory monitoring device. Such signals are typically used by the pulse sequence server 110 to synchronize, or "gate," the performance of the scan with the subject's heart beat or respiration.

The pulse sequence server 110 also connects to a scan room interface circuit 132 that receives signals from various sensors associated with the condition of the patient and the magnet system. It is also through the scan room interface circuit 132 that a patient positioning system 134 receives commands to move the patient to desired positions during the scan.

The digitized magnetic resonance signal samples produced by the RF system 120 are received by the data acquisition server 112. The data acquisition server 112 operates in response to instructions downloaded from the operator workstation 102 to receive the real-time magnetic resonance data and provide buffer storage, such that no data is lost by data overrun. In some scans, the data acquisition server 112 does little more than pass the acquired magnetic resonance data to the data processor server 114. However, in scans that require information derived from acquired magnetic resonance data to control the further performance of the scan, the data acquisition server 112 is programmed to produce such information and convey it to the pulse sequence server 110. For example, during prescans, magnetic resonance data is acquired and used to calibrate the pulse sequence performed by the pulse sequence server 110. As another example, navigator signals may be acquired and used to adjust the operating parameters of the RF system 120 or the gradient system 118, or to control the view order in which k-space is sampled.

The data processing server 114 receives magnetic resonance data from the data acquisition server 112 and processes it in accordance with instructions downloaded from the operator workstation 102. Such processing may, for example, include one or more of the following: reconstructing two-dimensional or three-dimensional images by performing a Fourier transformation of raw k-space data; performing other image reconstruction techniques, such as iterative, backprojection, deep-learning, or other reconstruction techniques; applying filters to raw k-space data or to reconstructed images; generating functional magnetic resonance images; calculating motion or flow images; and so on.

Images reconstructed by the data processing server 114 are conveyed back to the operator workstation 102. Images may be output to operator display 112 or a display 136 that is located near the magnet assembly 124 for use by attending clinician. Batch mode images or selected real time images are stored in a host database on disc storage 138. When such images have been reconstructed and transferred to storage, the data processing server 114 notifies the data store server 116 on the operator workstation 102. The operator workstation 102 may be used by an operator to archive the images, produce films, or send the images via a network to other facilities.

The MRI system 100 may also include one or more networked workstations 142. By way of example, a networked workstation 142 may include a display 144, one or more input devices 146 (such as a keyboard and mouse or the like), and a processor 148. The networked workstation 142 may be located within the same facility as the operator workstation 102, or in a different facility, such as a different healthcare institution or clinic. The networked workstation 142 may include a mobile device, including phones or tablets.

The networked workstation 142, whether within the same facility or in a different facility as the operator workstation 102, may gain remote access to the data processing server 114 or data store server 116 via the communication system 140. Accordingly, multiple networked workstations 142 may have access to the data processing server 114 and the data store server 116. In this manner, magnetic resonance data, reconstructed images, or other data may be exchanged between the data processing server 114 or the data store server 116 and the networked workstations 142, such that the data or images may be remotely processed by a networked workstation 142. This data may be exchanged in any suitable format, such as in accordance with the transmission control protocol (TCP), the internet protocol (IP), or other known or suitable protocols.

The above-described systems and methods can be used to generate motion-robust and/or motion-corrected images. As used herein these systems and methods may be referred to as MOTOR-MRI. In particular, referring to FIG. 2, a flow chart is provided setting forth some non-limiting example steps 200 of a method for producing MRI images in accordance with the present disclosure. At process 202, multi-shot or multi-session MRI data is acquired. More particularly, the data may be acquired by performing a multi-shot or multi-session MRI pulse sequence, such as using the system described with respect to FIG. 1. For example, the pulse sequence may be designed to acquire T2-weighted data. Some non-limiting examples of pulse sequences may include T2 FLAIR-, SWI-, DTI-, EPI-, and SSFP-based pulse sequences. Alternatively, the data may be acquired by accessing previously-acquired or stored MRI data. That is, the systems and methods described herein may be used to create improved images from previously-acquired data. Whether acquiring data form a patient or acquiring previously-stored data, the data acquired at process block 202 includes data acquired over multiple scan repetitions (e.g., repeated individual scans (RIS)), which may occur within the same acquisition session.

At process block 204, a candidate image reconstructed from the data and corresponding to one of the RIS is registered against a reference image. The images may be volumetric images. The registration may be a deformable registration, or another type of registration technique. At process block 206, the reference image and a candidate image are blended.

Figure 2:
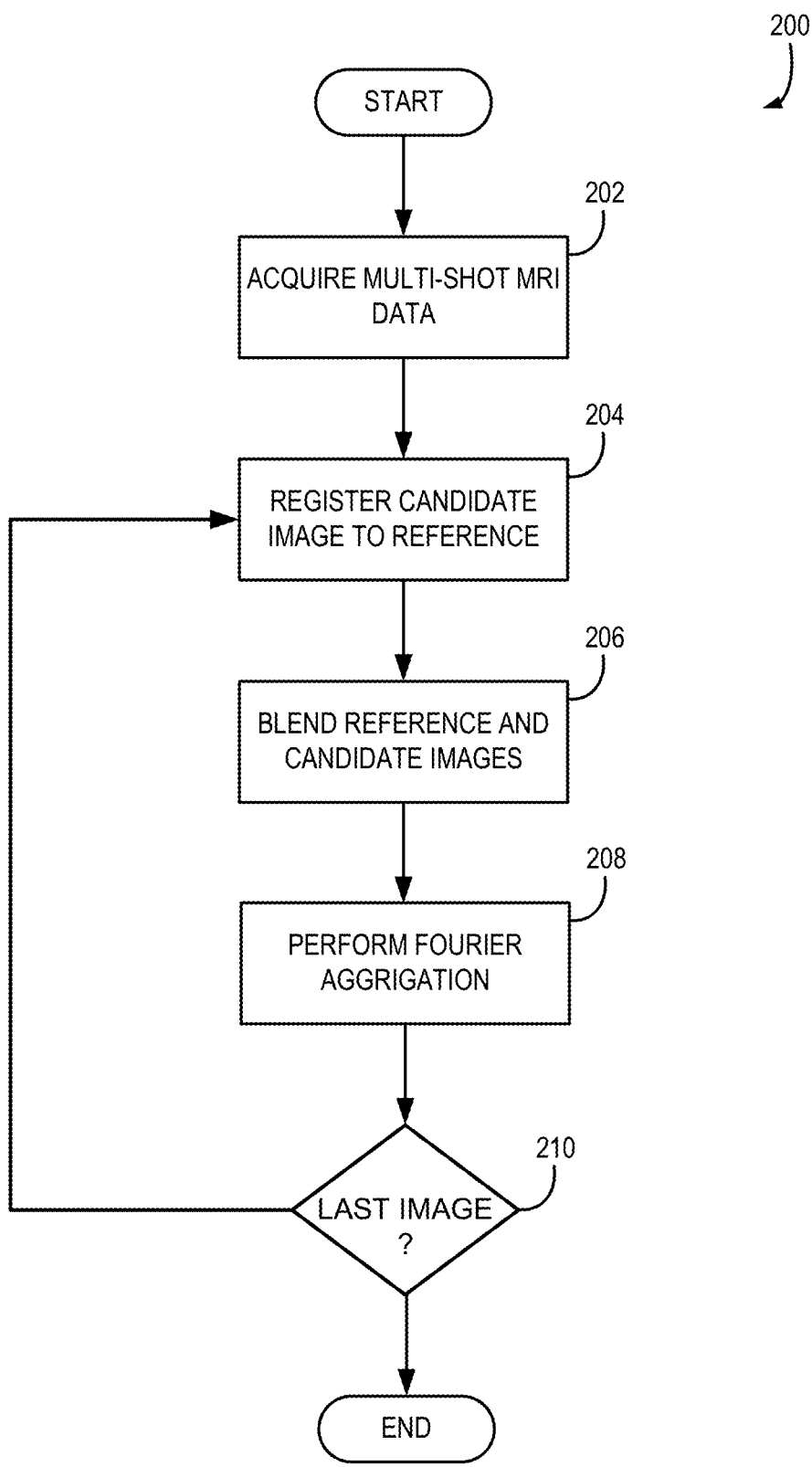
FIG. 2 is a flow chart setting forth some non-limiting examples of steps of a process in accordance with the present disclosure.
Figure 3A:
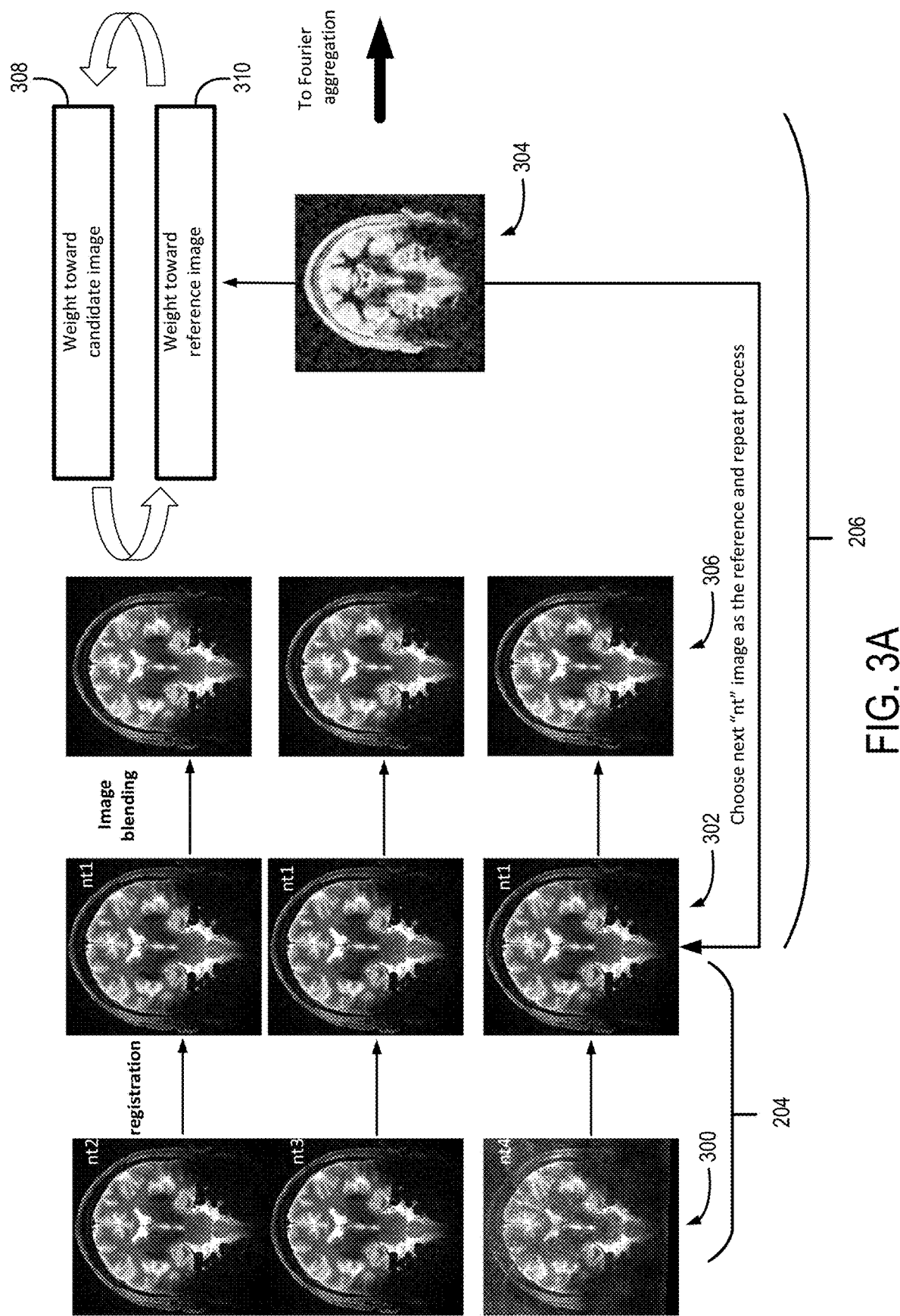
FIG. 3A is a graphic illustration of a portion of a motion control process in accordance with the present disclosure.

Referring to FIG. 3A, a graphic illustration of image registration at process block 204 of FIG. 2 and image blending at process block 206 of FIG. 2 is provided. In FIG. 3A, a series of candidate images are illustrated 300, with individual candidate images labeled as nt2, nt3, and nt4. Also a reference image 302 is illustrated and labeled nt1. As shown, each candidate image 300 is registered to the referenced image 302. Then, image blending can be performed using a consistency map 304.

The consistency map is utilized to select an algorithm to be used to generate a blended image 306. That is, the consistency map may be used as a threshold to choose between different weightings. To this end, as will be described, a variety of options may be used to select the consistency map. In one non-limiting example, the consistency map may be formed pixel-by-pixel using a forward and back analysis of images of the subject to produce a very-sharp, overall consistency map. That is, the consistency map can be created by performing a forward+backward registration between each candidate image and the reference image. More particularly, in one configuration, for each candidate image and the reference image, the process includes a registration and calculation of the pixel-wise displacement between original pixels and resulting ones. For each new image that is considered as a reference image, this process repeats until all images have been the reference image. For example, a pixel may be considered consistent if the forward+backward pass is less than a predefined threshold, such as will be further described with respect to FIG. 7. A Gaussian function, or any other smoothing kernel, may then be applied to blur the sharp consistency map to make the blending smoother.

Furthermore, the consistency map may be used in a variety of different ways to serve as the threshold, which is another threshold that may be distinct from the threshold described above for assessing pixel consistency. As one non-limiting example, an entropy calculation may be performed for a given candidate image against the consistency map. Alternatively, general variance may be evaluated, or a structural similarity index (SSIM) may be used, or any other intrinsic, calculable property of the consistency maps. Furthermore, a variety of algorithms may then be used to determine how to weight the blending based on the analysis of the candidate image relative to the consistency map.

In one non-limiting example, two algorithms 308, 310 may be provided to allow selection between weighting the blended image toward the candidate image or weighting the blended image toward the reference image. In one non-limiting example, the first algorithm 308 may create a blended image by multiplying the consistency map with the candidate image and then adding the inverse of the consistency map (i.e., 1-consistency map) multiplied by the reference image. As another non-limiting example, the second algorithm 310 may switch the reference and the candidate image, to weight toward the reference image instead of the candidate image. That is, the consistency map may be multiplied by the reference image. Then, the inverse of the consistency map (i.e., 1-consistency map) may be multiplied by the candidate image. Thus, in this case, the candidate map is used to identify motion in the reference image. In one non-limiting example, the process may be iterative. In a first iteration, multiple consistency maps may be calculated (even all possible consistency maps). Then, based on the collection of consistency maps, a threshold can be determined. For example, the threshold can be determined from the entropy per all slices from all consistency maps. Then, a label can be assigned to each image (or even each slice within each volumetric image). This label can be, for example, either sharp or motion corrupted. Then, based on a truth-table or any other selection rule, the blending (straight or reversed) can be performed. A user may provide input to select a preference for increasing signal-to-noise ratio, or motion robustness.

Figure 3B:
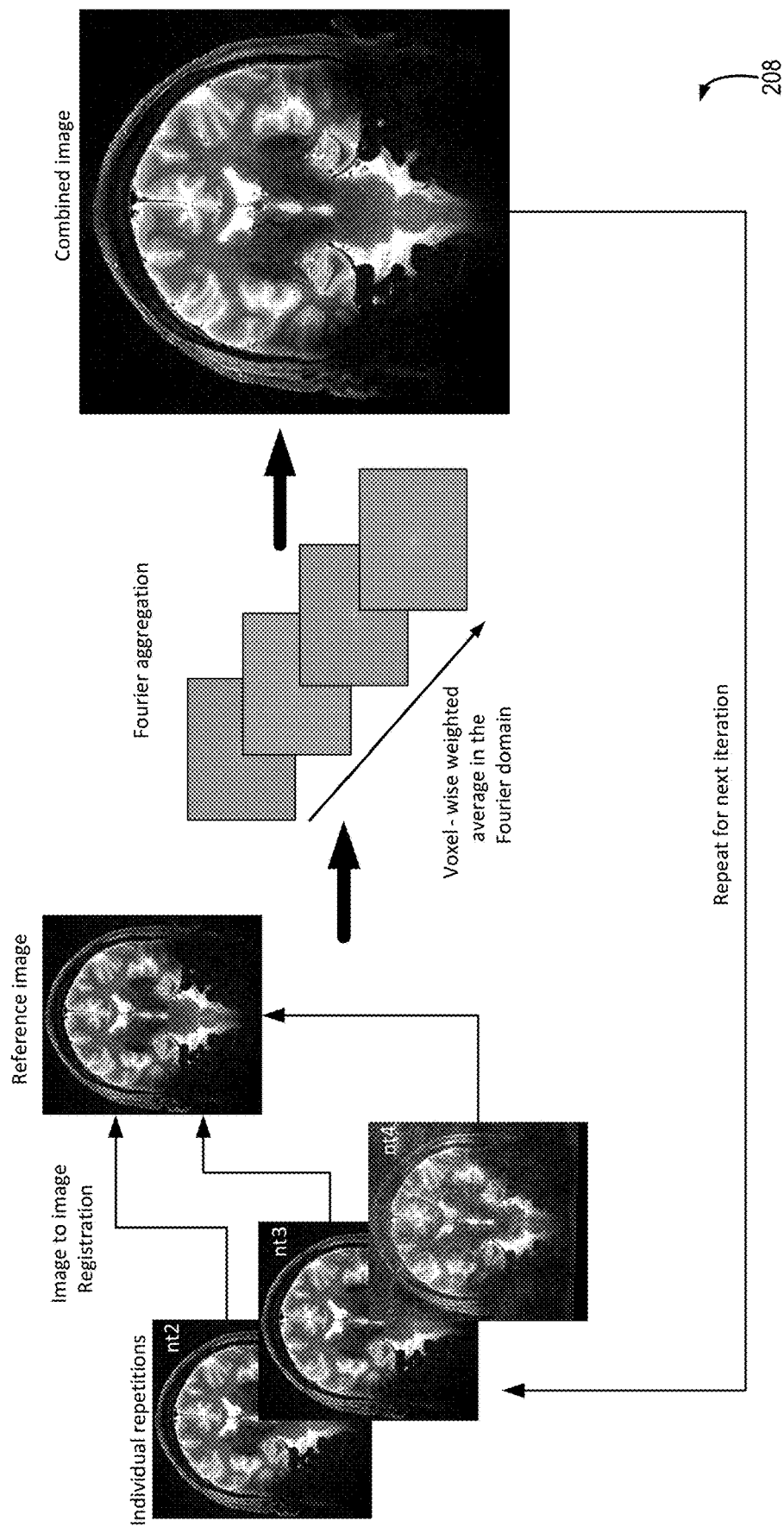
FIG. 3B is a graphic illustration of a further portion of the motion control process in accordance with the present disclosure.

Referring again to FIG. 2, at process block 208, Fourier aggregation is performed. That is, once the blended images are created for each candidate image or slice, the process continues to Fourier aggregation 208, at FIG. 3B. A voxel-wise weighted average is performed in the Fourier domain, that is a Fourier aggregation, that yields a combined image. The combined image is iteratively generated for each scan (volume)/slice.

Referring again to FIG. 2, the above-described process can be performed for each image (volumetric) or on a "slice-by-slice" basis. As described above, selection can be done based on the variance of the entropy values obtained from the consistency maps, or by any other decision mechanism.

At decision block 210, if the last image has not been processed, the system iterates for the next image/slice. This above-described process and any computer system, computer program, or other systems can be referred to herein as MOTOR-MRI.

Figure 4:
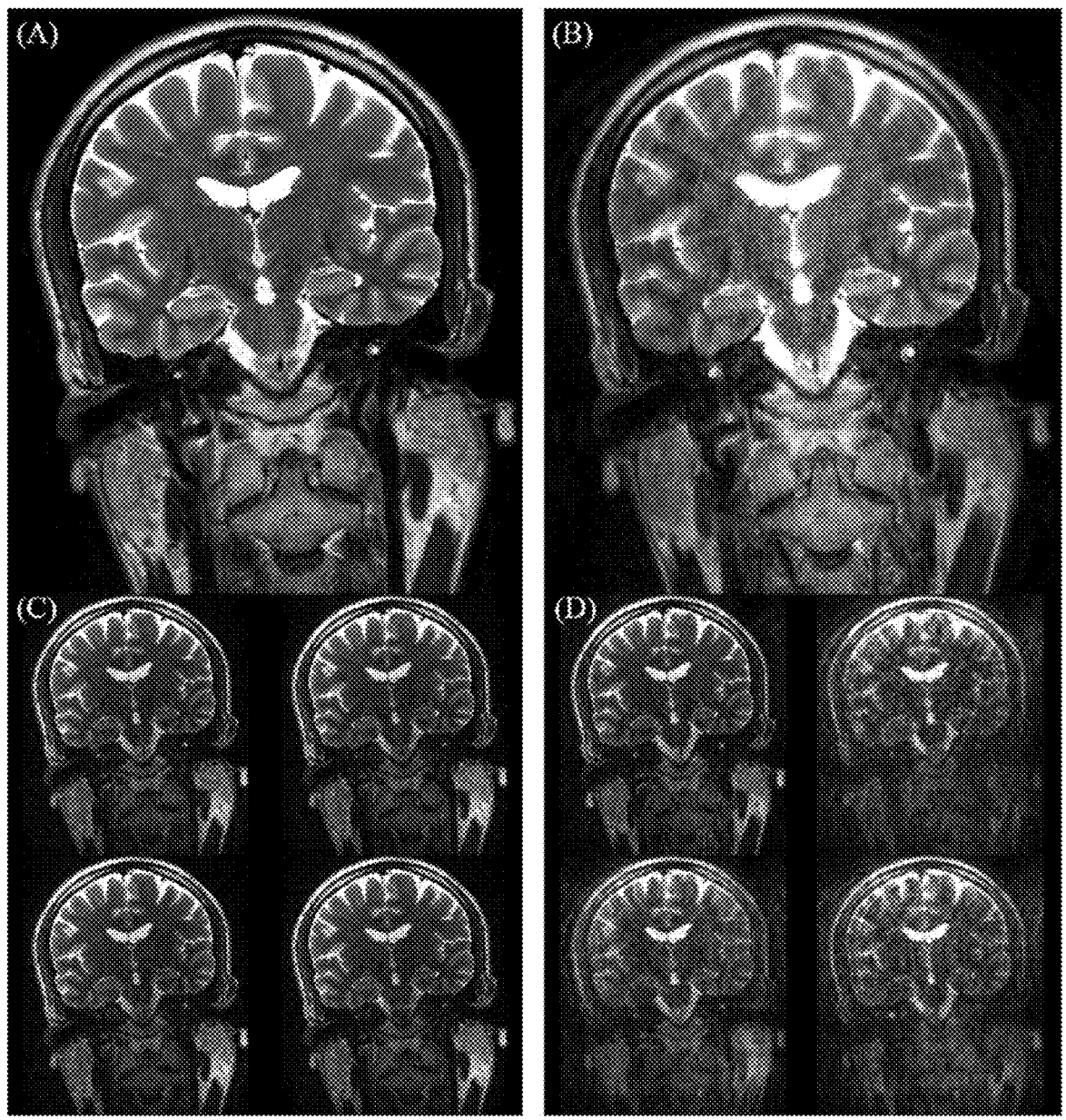
FIG. 4 is a collection of correlated images showing sharp versus motion affected MRI images demonstrated on T2-weighted coronal brain imaging. In image (A), a sharp MR image is produced by the scanner when the subject lies motionless. In image (B), the subject moves during the scan, and the resulting image is often blurred and includes unique MR-artifacts such as ringing artifacts. In image (C) a 2×2 block of four individual repetitions acquired to generate image (A) are shown. In image (D) a 2×2 block of four individual repetitions acquired to generate image (B) are shown.

To further illustrate the aspects of MOTOR-MRI, non-limiting examples will be considered. Referring to FIG. 4, two sets of correlated images are shown, where images (A) and (B) show the resulting T2-weighted coronal brain images from five individual repetitions for the same subject, produced on a 3 T scanner. In this case, in image (A), the subject did not noticeably move during the acquisition process and thus the image is sharp and clinically usable. However, in image (B), there was patient motion during the data acquisition, such that the image, which was reconstructed using traditional image reconstruction techniques, is blurred and, possibly, not clinically usable. For the images in images (A) and (B), four of the five low SNR images are shown in images (C) and (D), respectively. While the individual images are consistent across image (C), the images in image (D) are noticeably blurred and noisy and, most importantly, have apparent motion artifacts. This poor image quality may lead to false diagnosis or sub-optimal surgical planning.

The systems and methods of the present disclosure, MOTOR-MRI, recognize that the repeated acquisitions of images of identical anatomical structures and of different quality, as in standard MRI acquisition clinical protocols, often has the necessary acquired information to obtain high-SNR and high-quality data. More particularly, as will be described, a Fourier based aggregation (FBA) is used, for example, to reduce or remove image blur and noise. The FBA assists with the automatic detection of region-based "lucky frames" or "lucky views", regions in either image or frequency domain, where local parts of a globally blurry image appear sharp, for example, in different exposures/repetitions. Since motion induced blur is random by nature, not all images are equally blurred. Thus, this local sharp information can be used to substitute blurred regions with sharp ones to produce a globally sharp image. MOTOR-MRI expands this concept to volumetric MRI scans, with a special emphasis on the fact that motion in MR acquisitions is manifested in a different manner than other images, such as those produced, for example, by a hand-held camera. As provided herein, a careful combination of the weighted averaging process of the FBA algorithm and a discrimination mechanism provides an efficient motion artifact suppression scheme for MRI.

In MOTOR-MRI, image enhancement is not based on sub-optimal image models, but on physically accurate models of the actual degradation process. As described herein, x represents a scalar and $\vec{X}$ represents a vector. The notation a⊗b represents the convolution between a and b, a·b represents the composition of a and b, and F represents the Fourier transform operator.

The idea of FBA for blur removal in photographic devices relies on the acquisition of a burst of images, such that the motion blur in each image in the sequence is random (due to the random, naturally occurring hand-shakes of the camera holder). The standard acquisition model for a single image can be written as:

$$v_i = u_i \otimes k_i + n_i, i \in [0, \ldots, N] \quad \text{Eqn. (1)};$$

where i is the image index in a set of N acquired images $v_i$, $u_i$ is the $i^{th}$ sharp and noiseless image, $k_i$ is the $i^{th}$ random and unknown motion blur kernel, and $n_i$ is the $i^{th}$ additive white noise realization. Note that, in general, this problem is a non-trivial one, because the deblurring algorithm must handle the dynamics of the captured scene and the unknown kernel and noise. Instead of trying to model this complex problem with a model that considers all of the different dynamic factors, in FBA, the underlying image is deblurred by locally fusing consistent information present in the frames $v_i$.

Assume that without loss of generality, the blur kernels are non-negative and normalized as:

$$\int k_i(x) dx = 1, i \in [0, \ldots, N] \quad \text{Eqn. (2)}.$$

Given a set of N images, one of which arbitrarily denoted as the reference image with index i=0, equation (1) can further be written as:

$$v_i = u_0(\tau_0^i) \otimes k_i + o_i + n_i, i \in [1, \ldots, N] \quad \text{Eqn. (3);}$$

where $u_0$ is the latent sharp reference image, $\tau_0^i$ is a geometric transformation between the $i^{th}$ image and the reference image, $o_i$ represents parts in the $i^{th}$ image, which are different from the reference image (e.g., a moving car or occlusions), and we have omitted the 2D coordinates x for brevity (i.e., used $\tau_0^i$ instead of $\tau_0^i(x)$).

To handle the dynamic nature of a captured scene with occlusions, and to be able to perform a correct weighted average of the images in the sequence, the images first need to be registered to one another. Although many registration approaches exist, one non-limiting example for the FBA algorithm relies on the estimation of the optical flow field between a reference image ($v_0$) and the rest of the captured images in the sequence $v_i$, $i \in [1, \ldots, N]$.

Note that, generally, due to occlusions, the resulting flow field from the registration of one image to another is different than the estimated flow field when registration is performed in the opposite direction. Consider the reference image $v_0$ and another image from the sequence, denoted as $v_i$, $i \in [1, \ldots, N]$. Let $\tau_0^i$ be the estimated flow field from $v_i$ to $v_0$, and $\tau_i^0$ be the reverse estimated flow field from $v_0$ to $v_i$. Consider, then, the following difference:

$$cMap_i(x) = |(\tau_i^0 \cdot \tau_0^i)(x) - x| \quad \text{Eqn. (4).}$$

A pixel x is said to be consistently registered if $cMAP_i(x) \leq e$, where e is a predefined consistency threshold. Now define a consistency mask $m_i(x)$, such that $m_i(x)=1$ if x is consistent and 0 otherwise. The consistent, or blended, version of $v_i$ now takes the form of:

$$\tilde{v}_i^0(x) = m_i(x) v_i(\tau_i^0(x)) + (1 - m_i(x)) v_0(x) \quad \text{Eqn. (5)}$$

In practice $m_i(x)$ is smoothed with a small Gaussian kernel to produce smoother transitions between the two images and avoid artifacts. The optical flow field can be performed iteratively and with multiple resolution scales via the algorithms detailed in C. Zach, T. Pock, and H. Bischof, \A duality based approach for realtime tv-l1 optical flow," in Joint pattern recognition symposium. Springer, 2007, pp. 214-223 and J. S. Perez, E. Meinhardt-Llopis, and G. Facciolo, \Tv-l1 optical flow estimation," Image Processing On Line, vol. 2013, pp. 137-150, 2013, each of which is incorporated herein by reference. Though any of a variety of methods of registration can be utilized.

This process is repeated for each image in the sequence, such that at the end of this process all N images are consistently registered to the reference image $v_0$. Once this process is done, the reference and registered images can be weighted averaged together; properly defining the weights is at the essence of FBA. From equation (2), it can be derived that the blur has all entries less than one, so all frequencies are attenuated. Since the blur kernels are random across the acquired images $v_i$, the frequency attenuations are random as well. Thus, selecting the largest or least attenuated value amongst the images in the sequence at each frequency point will lead to a sharp image estimate of $v_0$. In other words, a sharp image is obtained by picking, for each frequency point, the highest value in the series. In practice, and since each image is attenuated to some degree, it is better to perform a weighted average in each frequency, with weights based on the magnitude value of each image at that frequency (the higher the value the larger the local weight). This weighted average is written as:

$$\bar{u}(x) = F^{-1}\left( \sum_{i=0}^{N} \omega_i(\xi) F(\tilde{v}_i)(\xi) \right); \quad \text{Eqn. (6)}$$

where the weights are given by:

$$\omega_i(\xi) = \frac{|F(\tilde{v}_i)(\xi)|^p}{\sum_{j=0}^{N} |F(v_j)(\xi)|^p}; \quad \text{Eqn. (7)}$$

and p is a weighting factor. If p=0, then equation (6) is a standard arithmetic average of the images and, if p→∞, from equation (6), the highest frequency component at each frequency & along the sequence is selected.

This process can be repeated, to further improve the results. Each image in the sequence 0, ..., N can be considered as the reference image, such that the other images in the sequence are registered to it and consequently averaged via equation (6) and equation (7). When this process is finished, the algorithm outputs a new sequence of N+1 Fourier aggregated images. To improve the estimation, this process can then be repeated iteratively, where the FBA generated images now serve as inputs.

While producing state of the art performance for handheld cameras, there is a major drawback in the FBA method when applied to MR acquisitions. For example, motion artifacts in MRI cannot be adequately modeled as a sharp, latent image convolved with a blur kernel. Moreover, artifacts are not mere occlusions. For example, a moving car in a burst sequence of images is still a part of the sequence, only in different positions within the burst. In MRI, these non-blur artifacts need to be removed altogether, or at least heavily mitigated. The main limitation of the FBA algorithm is its inherent symmetry when blending every two sets of images in the sequence. At each iteration, eventually all images in the acquisition sequence are used as reference, both sharp and motion corrupted ones. However, the systems and methods provided herein determined ways to utilize the virtues of FBA, while addressing this limitation and adapting it to MRI data.

Consider equation (3), where $o_i$ represents occlusions present in the $i^{th}$ image and not in the reference image. Such occlusions are not directly applicable to MR imaging. Instead, we define $o_i$ as imaging artifacts, present in the $i^{th}$ image, for example the artifacts, which are clear in image (B) of FIG. 4 in the cortex region.

Figure 5:
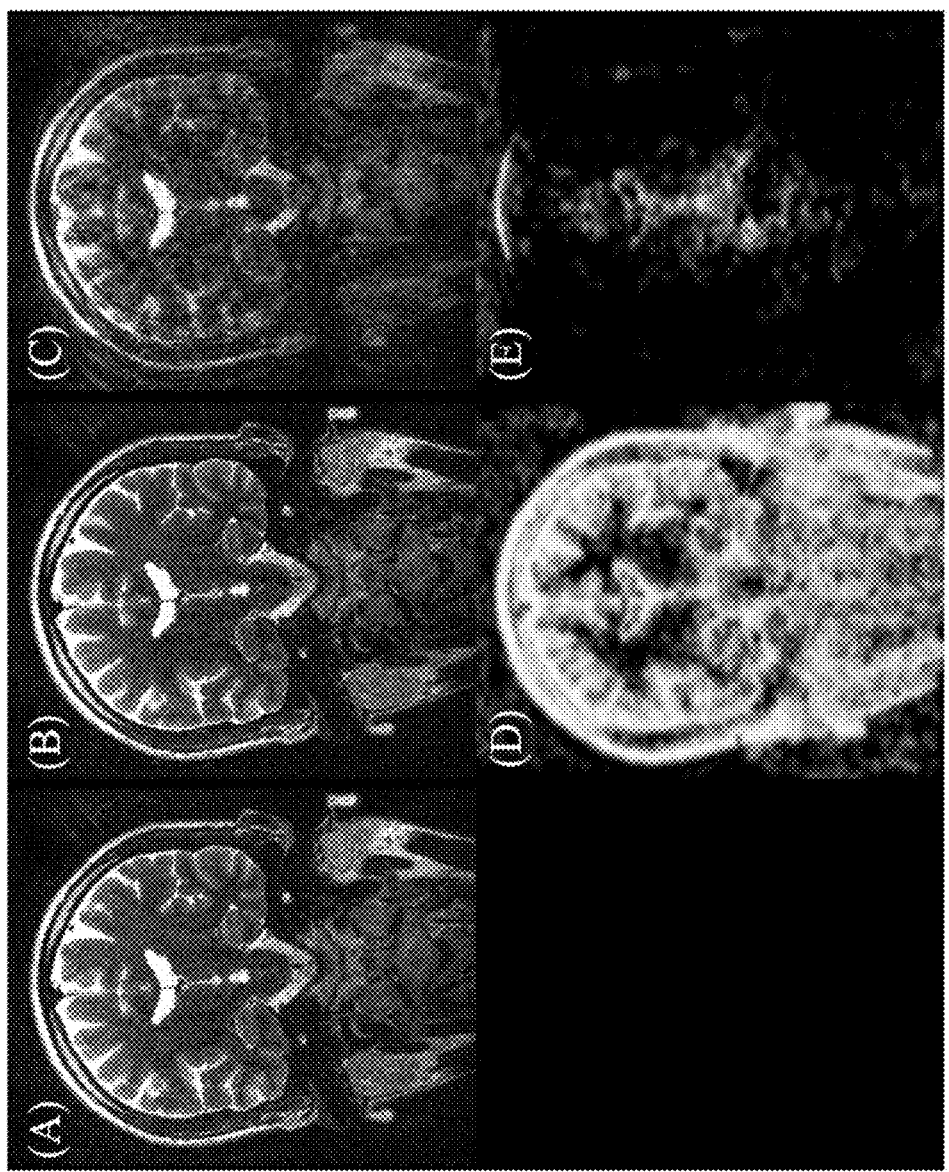
FIG. 5 is a collection of correlated images showing consistency maps between sharp and motion corrupted images. In image (A), a reference image with relatively few motion artifacts ("sharp") is shown. In, image (B) another sharp image in the sequence is shown. In image (C), a heavily motion-corrupted image from the sequence is shown. In image (D), a consistency map produced by the forward+backward registration process for image (A) and image (B). In image (E), a consistency map produced by the forward+backward registration process for image (A) and image (C).

Consider images (A)-(C) in FIG. 5. In this example, image (A) is considered for the moment as the reference image and images (B) and (C) are other images from the same acquisition series which need to be registered to (A) ("candidate" images). Here, both images (A) and (B) have little artifacts (and will be referred to from hereon as "sharp" images), while image (C) is heavily affected by severe motion artifacts and blur. Now, image (D) presents the consistency map produced by equation (4) between images (A) and (B), while image (E) shows the consistency map produced by equation (4) between images (A) and (C) (after the application of a smoothing Gaussian kernel). Based on these consistency maps, the blended image from registering (B) to (A) will mostly be taken from image (B). However, based on the consistency map in (E), most of the information in the resulting blended image from registering (C) to (A) will be taken from (A). This indeed will result in the mitigation of most of the imaging artifacts in the blended image. However, when it is the turn of image (C) to become the reference, most of the information for the blended image will actually be taken from the corrupted image (C) (being the current reference) and not from the sharp image (A), as the consistency maps will be similar. Thus, eventually, due to this inherent symmetry, there will be a preservation of the imaging artifacts. The systems and methods provided herein, MOTOR-MRI, can break this symmetry, such that the artifacts are heavily mitigated.

A mechanism may be used to break this symmetry, which may be applied only at the first iteration. The mechanism can be automatic, rely only on the currently acquired sequence, and be sufficiently non-complex to implement and execute. Specifically, the present disclosure determined that a discrimination mechanism can be used, for example, to classify each image as sharp or corrupted. Thus, given reference image j, a candidate image i and a consistency map $m_i^j(x)$ between them, when blending every pair of images, an algorithm can be created that decides whether to use the original FBA blending equation, $$\tilde{v}_i^j(x) = m_i^j(x) v_i(\tau_i^j(x)) + (1 - m_i^j(x)) v_j(x) \qquad \text{Eqn. (8);}$$

or reverse the roles of the reference and candidate image and perform blending, $$\tilde{v}_i^j(x) = m_i^j(x) v_j(x) + (1 - m_i^j(x)) v_i(\tau_i^j(x)) \qquad \text{Eqn. (9).}$$

To decide, we rely on an intrinsic property of the consistency maps produced by equation (4) and exemplified in images (D) and (E) of FIG. 5.

Note, if two images are "similar" (i.e. both images are sharp, or with very few imaging artifacts), their joint consistency map will contain many consistent regions, such as the map presented in image (D) of FIG. 5. On the other hand, when presented with a motion corrupted image against a sharp one, the consistency map is very sparse, such as the one illustrated in image (E) of the same figure. Thus, by relying on the resulting consistency maps between each pair of images we can discriminate between heavily corrupted images and cleaner ones.

Figures 6A, 6B:
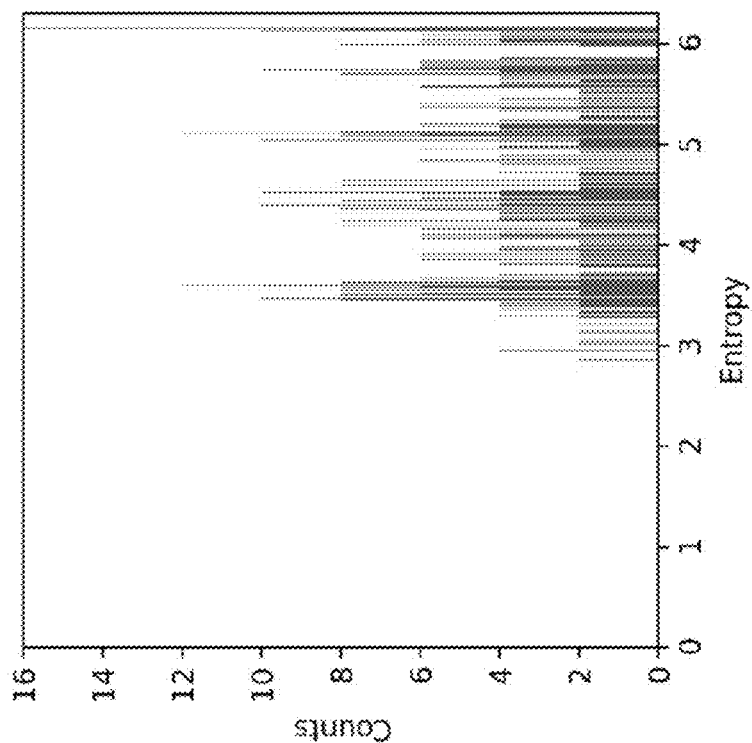
FIG. 6A is an entropy-based histogram of a sequence without any apparent motion is shown.
FIG. 6B is an entropy histogram of a sequence with apparent motion provided.

For each image out of the N+1 images acquired in the sequence, we calculate N consistency maps; each consistency map i is used in the blending operation between the $i^{th}$ candidate to the $j^{th}$ reference image. To perform discrimination, we calculate for each consistency map its entropy per each slice/image. The entropy of a discrete random variable q is defined as:

$$E = -\sum_{l=0}^{L} p(q_l) \log p(q_l); \qquad \text{Eqn. 10}$$

where $q_i$ represents different random realizations of q and $p(q_i)$ is the probability of the $l^{th}$ value. In the context of images, $q_l$ represent different grayscale values l=0, . . . , L, obtained by calculating its (1D) histogram with L bins. FIGS. 6A and 6B show two examples of the entropy histogram from a set of consistency maps of a sequence acquired without any noticeable motion (corresponds to image (A) of FIG. 4) and a sequence of images with significant motion (corresponds to image (B) of FIG. 4), respectively.

For each consistency map, a single representative entropy number is calculated by simply averaging all entropy values from each slice. Thus, each consistency map (and in effect, each candidate image i) is associated with a single number. Next, the algorithm computes an adaptive threshold based on the entropy histogram to perform discrimination. This threshold represents a percentage of the largest histogram values (e.g., one can use 10%, which was used in the experiments described herein). If an associated averaged entropy value of a candidate image is higher than this threshold, the image volume is deemed as sharp, and if not it is deemed motion corrupted. If no image was deemed as sharp, the algorithm blending defaults to the original FBA algorithm. After each candidate (and reference) image are labeled, the final blending decision is based on the logic in Table 1.

TABLE 1

Decision table for image blending.

| Reference | Candidate | Action |
|---|---|---|
| Sharp | Sharp | Equation (8) |
| Sharp | Corrupted | Equation (8) |
| Corrupted | Sharp | Equation (9) |
| Corrupted | Corrupted | Reject |

That is, if the reference image is sharp, blending is performed via equation (8). If the reference is motion corrupted but the candidate is sharp, the motion-corrupted image can be salvaged by blending using equation (9). If both images are motion corrupted, this pair can be rejected altogether and no blending performed. Since the acquired images are 3D volumes, the same logic can be applied per each slice in each volume. Thus, blending can be performed in a slice-by-slice rather than volume-by-volume manner, which in scans affected by severe motion allows for greater sensitivity in the classification process. In practice, if the variance of the entropy values (FIGS. 6A and 6B) is above, for example, 0.1, blending each slice individually can produce improved results than when blending volume-by-volume. If the variance is below this threshold, blending can be performed volume-by-volume, as described before.

At the end of the first iteration, histogram equalization can be applied to the resulting images via intensity re-scaling for better visual interpretation (between the 10th to 98th percentiles). At the end of the algorithm run, the final image is selected as the MOTOR-MRI image which corresponds to either the first image classified as sharp at the first iteration (volume-by-volume), or the image with the highest number of sharp slices (slice-by-slice). Lower entropy is associated with higher visual quality and reduction in motion artifacts. Thus, the image with the lowest entropy score (or any other decision criteria) can be selected.

Non-Limiting Example Experiments

Subjects were scanned on two 7 T MRI scanners (Magnetom Actively Shielded and Magnetom Terra, both 7 T Siemens, Erlangen, Germany). The 7 T Terra scanner was recently granted FDA approval for clinical diagnostic brain imaging. Both scanners are equipped with SC72 gradients capable of 70 mT/m and a 200 T/m/s slew rate using a 32-element head array coil (Nova Medical, Inc., Burlington, MA, USA). Whenever subject head size enabled enough space in the coil, dielectric pads were used to enhance signal in the temporal regions. The scan protocol included either a T2-weighted axial slab with 0.39×0.39×1 mm³ resolution and covering from the top of the thalamus to the bottom of the substantia nigra, or a coronal slab with 0.39×1×0.39 mm³ resolution and covering from the anterior commissure to the $4^{th}$ ventricle. Both axial and coronal slabs were acquired using a 2D turbo spin echo (TSE) sequence with the following image parameters: Field of view (FOV): 200×200×26 mm³; 512×512×26 matrix (0.39×0.39×1.0 mm³), TR/TE 9000/58 ms, flip angle=150 degrees, echo train length (ETL): 11, acceleration factor of 3 (GRAPPA) along the anterior-posterior (AP) and RL phase encoding directions for axial and coronal orientation, respectively; number of repetitions RIS, N=4 or 5. The number of slices was optimized manually for each subject in order to maximize spatial coverage of the mid-brain while minimizing acquisition time. The total acquisition time was around 7 minutes for each T2-Weighted scan (about 1.75 minutes per RIS).

Additional subjects were also scanned at 3 T (Magnetom Prisma 3 T Siemens, Erlangen, Germany) with a 32-channel head coil (Siemens, Erlangen, Germany). A whole-brain T2 TSE volume with 0.43×0.43×2.6 mm resolution was acquired with the following parameters: FOV: 220×179×177 mm, Orientation: coronal, 512×476×68 matrix, TR: 11.89 s, TE: 100 ms, ETL: 15, acceleration factor: 3 (GRAPPA), Phase encode (PE) direction: right to left. Acquisition time for 5 repetitions was approximately 9 minutes (about 1.8 minutes per RIS).

To perform quantitative analysis, we also acquired several T2-weighted TSE scans of a cadaver using a 7 T scanner in the following manner. First, we acquired a ground-truth scan with 10 completely motion-free repetitions, giving high accuracy and signal-to-noise ratio (SNR). We then acquired several scans with motion. Motion was introduced by physically rocking the cadaver's legs during the scan. We then combined the motion free and motion affected images into five sets of four images each, such that the number of motion affected images in each set increases. That is, the first set contains four images of motion-free images, the second set contains three motion-free images and one motion affected image and so on, until the last set contains four motion affected images. This study was approved by the Institutional Review Board at the University of Minnesota and all participants gave their informed consent.

Figure 7:
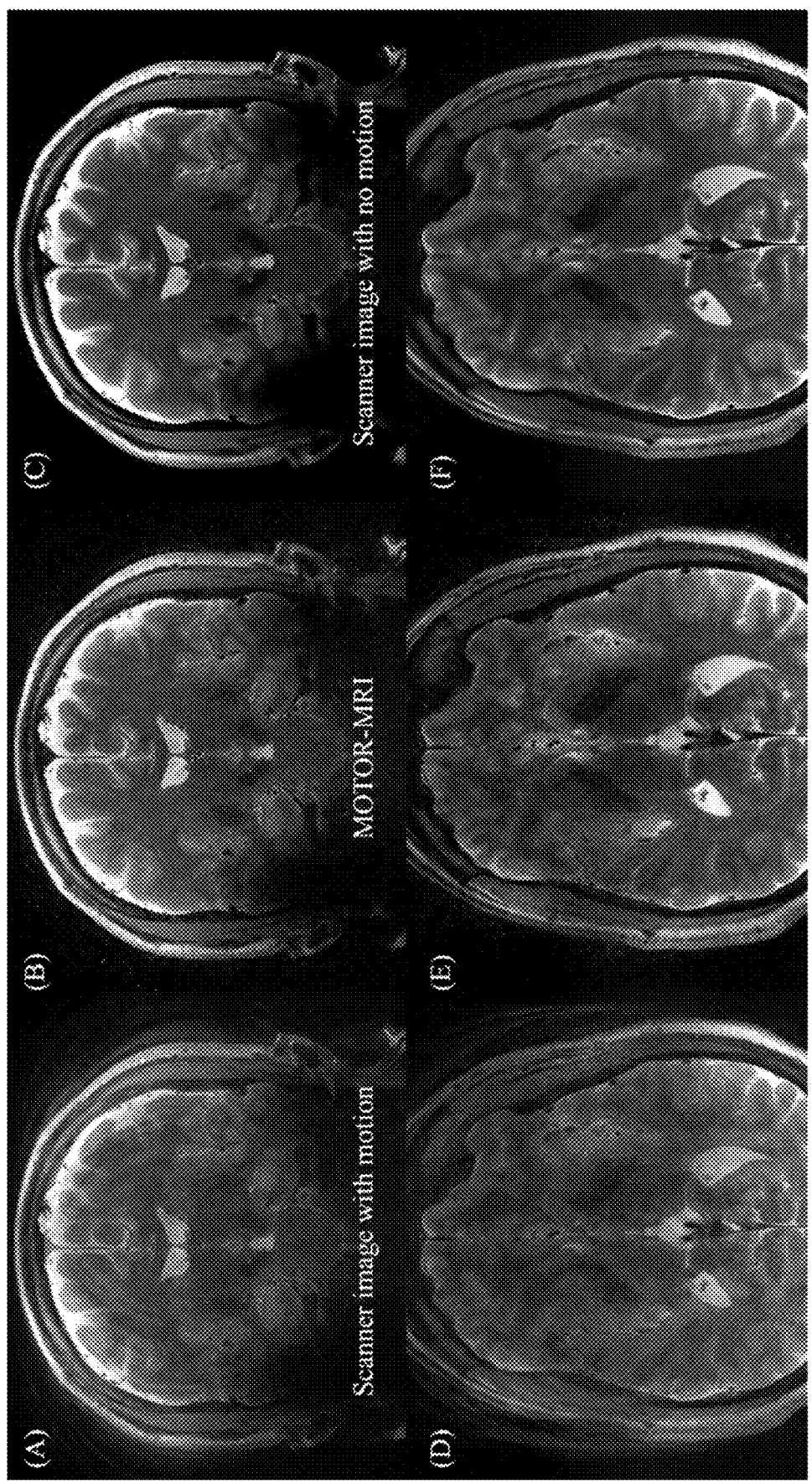
FIG. 7 is a set of correlated images where images (A)-(C) are 7 Tesla (T) coronal and images (D)-(F) are axial slabs, each produced with four repetitions. More particularly, image (A) and image (D) were produced using traditional reconstruction from data acquired during severe motion. On the other hand, image (B) and image (E) were produced using the system and methods of the present disclosure from the same data as in image (A) and image (D), respectively. Finally, image (C) and image (F) are images of repeated, motion-free scans.

We evaluate MOTOR-MRI on several T2-weighted TSE brain scans from multiple participants, scanned on 3 T and 7 T scanners. We start with an example which clearly demonstrates the ability of MOTOR-MRI to significantly mitigate motion artifacts and improve the contrast of the final image. FIG. 7 presents T2-weighted coronal and axial views taken from two 7 T scans, each comprised of four repetitions. Images (A) and (D) show the original data as the image produced by the scanner; images (B) and (E) present the images using a MOTOR-MRI process, using the same data that was used to generate the images in images (A) and (D), respectively. Images (C) and (F) show the scanner images from a second, motion free scan, also with four repetitions. The standard images in images (A) and (D) are clearly and dramatically affected by motion. Again, as can be seen in both images (B) and (E) using the exact same data, the processing of MOTOR-MRI mitigates this motion. Fine blood vessels and deep-brain nuclei are better observed in images (B) and (E), with clarity comparable to the motion-free images of images (C) and (F), respectively. On the other hand, these features are either non-visible or unclear in the motion affected images. This example demonstrates the ability of a process using MOTOR-MRI to remove significant blur and motion artifacts for arbitrary image orientations, and to salvage otherwise unusable images.

Table 2 summarizes the peak SNR (pSNR) for FIG. 7. For each image, the pSNR metric was calculated between either the motion affected scanner image and the motion-free scanner image or the MOTOR-MRI image and the motion-free scanner image. Observing Table 2, MOTOR-MRI produces higher pSNR scores by several dB, further demonstrating that MOTOR-MRI can salvage MR images under severe motion conditions and recover otherwise lost SNR due to motion.

TABLE 2

| pSNR values. Values in dB | | |
| --- | --- | --- |
| FIG. | MOTOR-MRI | Scanner Image |
| FIG. 7 - coronal | 25.15 | 21.3 |
| FIG. 7 - axial | 25.15 | 22.25 |

Figure 8:
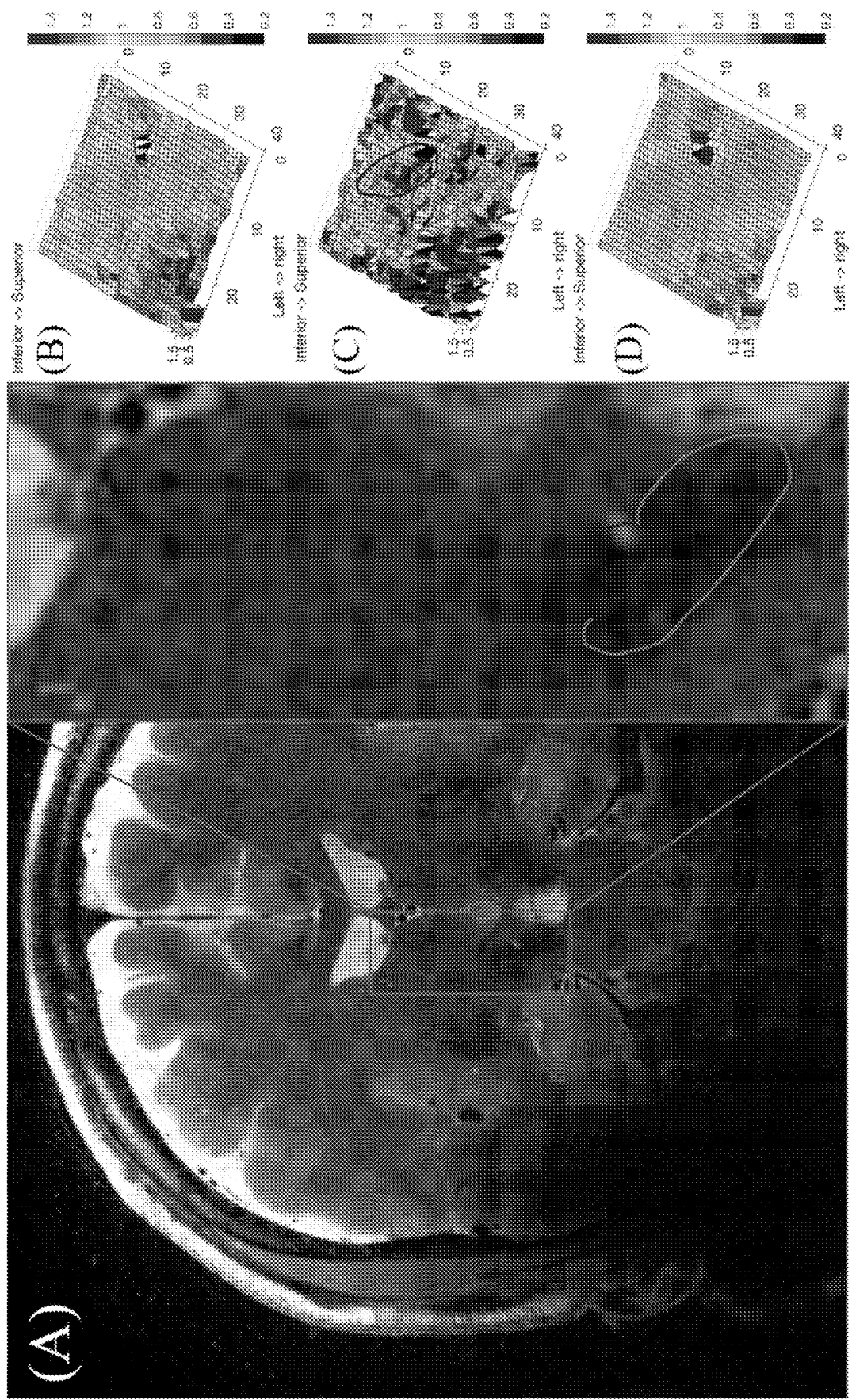
FIG. 8 is a set of correlated images and graphs illustrating contrast enhancement and improved visualization. In image (A), an image was produced using the systems and methods of the present disclosure of the same coronal slice shown in FIG. 7, image (B) with an enlarged region in red rectangle with outlined parts of the basal ganglia region. Graphs (B)-(D) provide surface plots of parts of the subthalamic nucleus (STN) and lateral edge of the substantia nigra (SN), corresponding to the same outlined regions as in image (A) and based on the motion corrupted image (FIG. 7, image (A)), MOTOR-MRI image (FIG. 7, image (B)), and motion free image (FIG. 7, image (C)), respectively. Color bars represent voxel grayscale values divided by the respective mean grayscale value of each image.

The example shown in FIG. 7 highlights another improvement of processes using MOTOR-MRI, even against non-motion affected images. Image (A) of FIG. 8 show the same image as image (B) of FIG. 7 with an enlarged region displayed within a red box. Images (B)-(D) present an objective evaluation of the contrast improvement produced by processes using MOTOR-MRI. Each image (B)-(D) is a surface plot of the subthalamic nucleus (STN) (marked with a blue outline) and a superior portion of the substantia nigra (SN) (marked with a purple outline) for the images in images (A)-(C) of FIG. 7, respectively. A clear identification and delineation of these two sub-cortical nuclei is of great importance to DBS surgery. However, their borders are often unclear, even without patient movement. Vertical intensity profiles were taken from each image (A)-(C) of FIG. 7 to produce surface plots. These surface plots visually illustrate the contrast differences between the different images and are scaled to the same intensity range.

Clearly, images produced using MOTOR-MRI (image (C)) have the largest contrast difference compared with both images (B) and (D). Table 3 presents contrast ratios (mean grayscale value from a 5×5 patch outside the STN/SN divided by the mean grayscale value from a patch of similar size within the STN/SN) from each of the images (B)-(D), which further supports this claim. Only images produced using processes based on MOTOR-MRI can clearly visualize the borders of the STN and SN. Thus, the process using MOTOR-MRI mitigates the effect of patient movement, but also improves image contrast and overall visibility, even when comparing against an image produced under ideal conditions.

TABLE 3

| Contrast ratio for each surface plot in FIG. 8, where values are in dB. | | |
| --- | --- | --- |
| Motion affected (B) | MOTOR-MRI (C) | MOTOIN FREE (D) |
| 2.91 | 4.66 | 3.83 |

Figure 9:
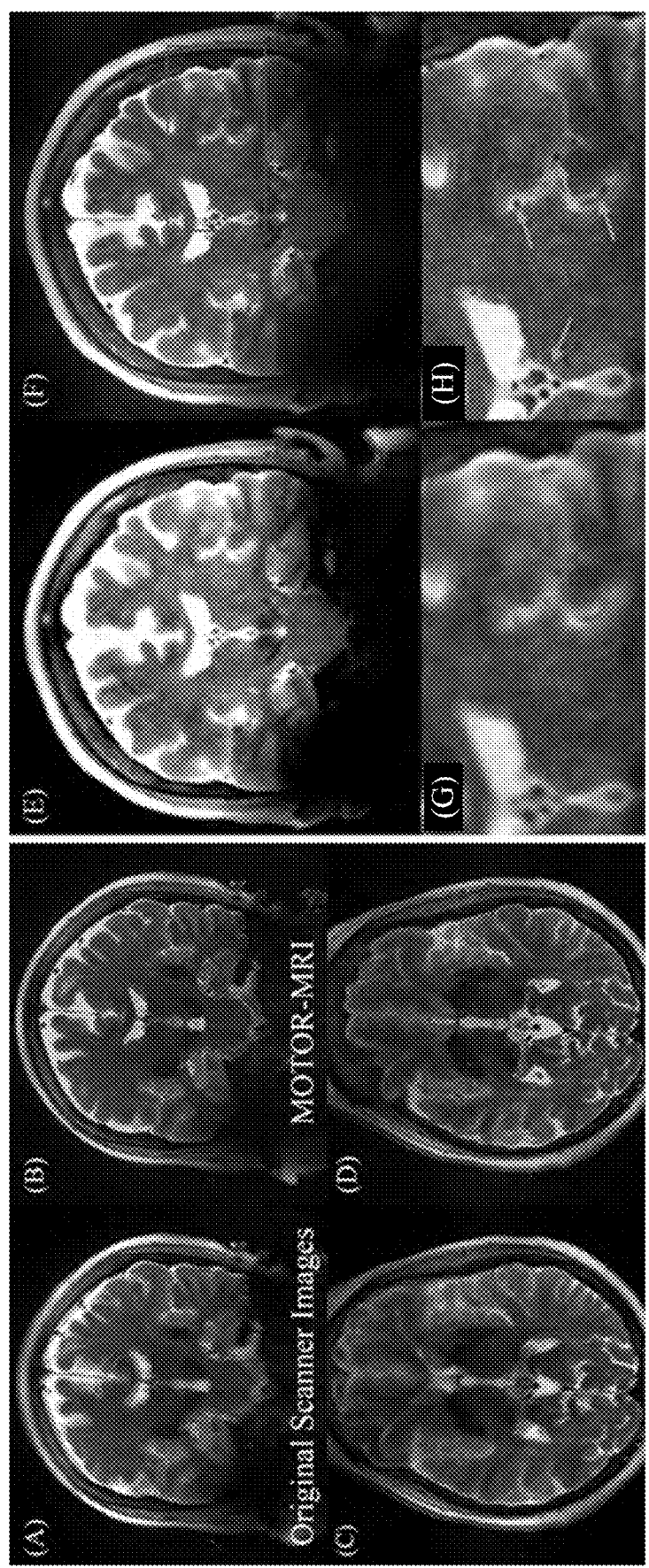
FIG. 9 is a set of correlated patient images of 7 T coronal slabs produced with four repetitions. In images (A) and (C), 7 T coronal and axial images are provided of an ET patient produced by the scanner with severe motion, respectively. Images (B) and (D) are corresponding MOTOR-MRI images produced from the same data as in (A) and (C), respectively. In image (E), the data was acquired during severe motion and the image was produced by the scanner using traditional reconstruction. In image (F), MOTOR-MRI reconstruction was used to produce the image from the same data as in image (E). In image (G) and image (H), enlarged regions are shown that correspond to the region marked by the rectangle from image (E) and image (F), respectively.

MOTOR-MRI can also improve image quality in a non-controlled scenario, in which actual patients are being scanned. FIG. 9 presents two cases of patients who were scanned on a 7 T scanner (4 RIS each), prior to DBS surgery at the medical center of the University of Minnesota. These T2-weighted images (coronal and axial orientations) are used to delineate sub-cortical nuclei within the brain which are used in surgery planning. Images (A) and (C) show coronal and axial orientation scans from an ET patient, respectively, with noticeable blur and ghosting effects. On the other hand, MOTOR-MRI images (images (B) and (D), respectively) are sharp and devoid of noticeable motion artifacts. Moreover, in both MOTOR-MRI images, sub-cortical nuclei (darker segments in the middle of the brain) appear sharp with clear borders, which are, as described before, important for several neurological applications.

Ringing/ghosting-like motion artifacts are not the only kind of image degradation in MR images. FIG. 9 presents an example of a T2-weighted coronal orientation obtained via a 7 T scanner with four repetitions. Image (E) shows a coronal orientation, which shows motion artifacts and in addition, noticeable image blur. Image (F) presents the corresponding MOTOR-MRI image, produced from the same data of image (A). Images (G) and (H) are enlarged regions, corresponding to the red rectangle in image (F), from images (E) and (F), respectively. The arrows in image (H) highlight blood vessels, which are obscured in the scanner produced image in images (E) and (G). MOTOR-MRI can effectively mitigate the motion artifacts, remove the image blur and in the process provide improved depiction of fine features such as blood vessels. Both FIGS. 8 and 9 exemplify MOTOR-MRI's ability to produce higher quality images, with efficient motion mitigation, both in a controlled motion experiment and in real life scenarios in which actual patients are being scanned.

Figure 10:
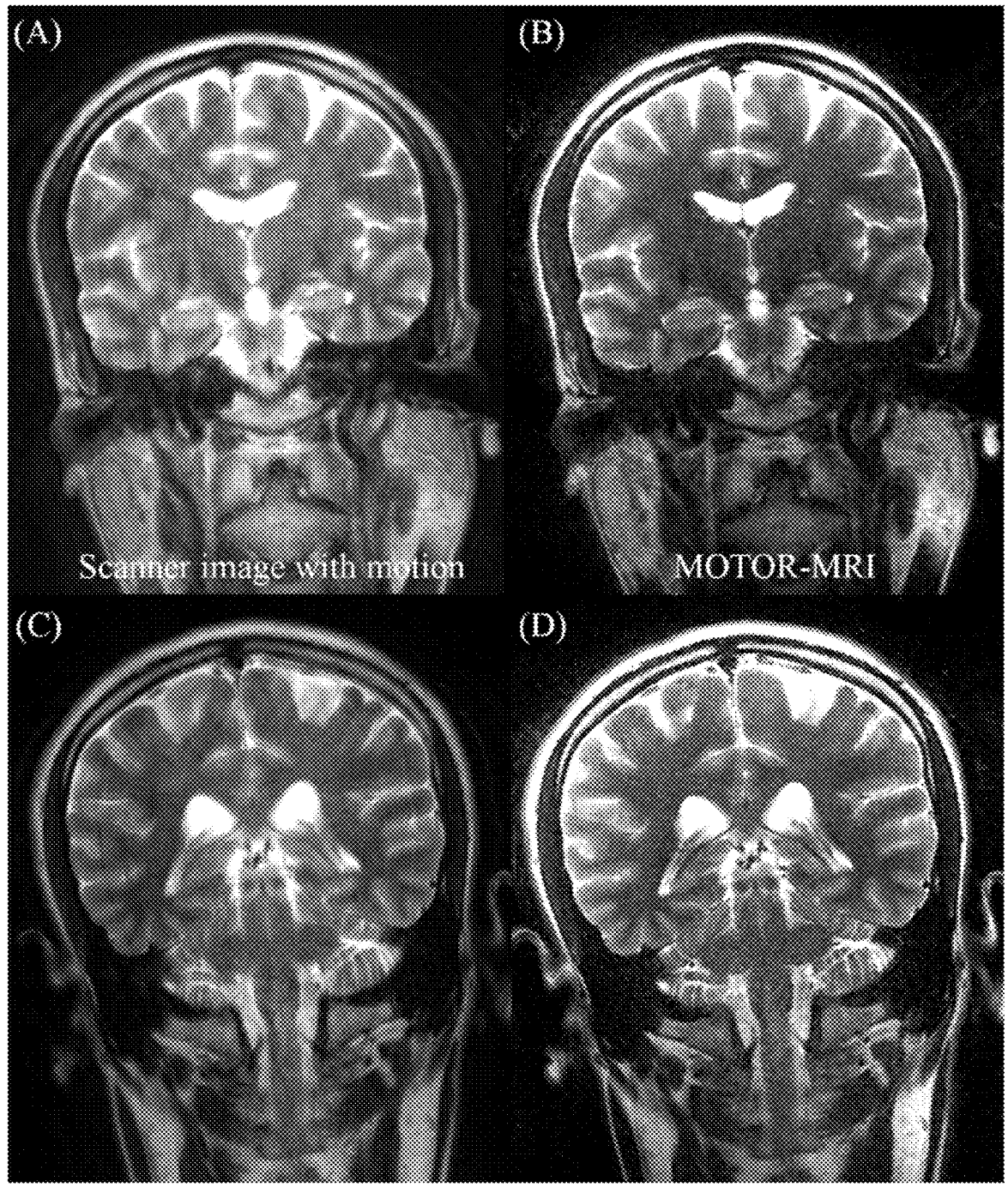
FIG. 10 is a set of correlated images of 3 T whole head scan produced with five repetitions (coronal projection presented). In image (A) and image (C), the images were reconstructed using traditional reconstruction from data acquired with severe motion. In image (B) and image (D), MOTOR-MRI was used to produce the images from the same data as in image (A) and image (C), respectively.

MOTOR-MRI is applicable to any type of scanner, including clinical systems. In FIG. 10, a 3T, T2-weighted, TSE whole brain scan was obtained with standard clinical acquisition parameters, as detailed below. Images (A) and (C) show original scanner images of two slices, while images (B) and (D) illustrate their MOTOR-MRI counterparts. In both images (A) and (C) motion artifacts are clearly visible, as well as noticeable image blur. These artifacts and blur are significantly mitigated in the MOTOR-MRI images in images (B) and (D).

Figure 11:
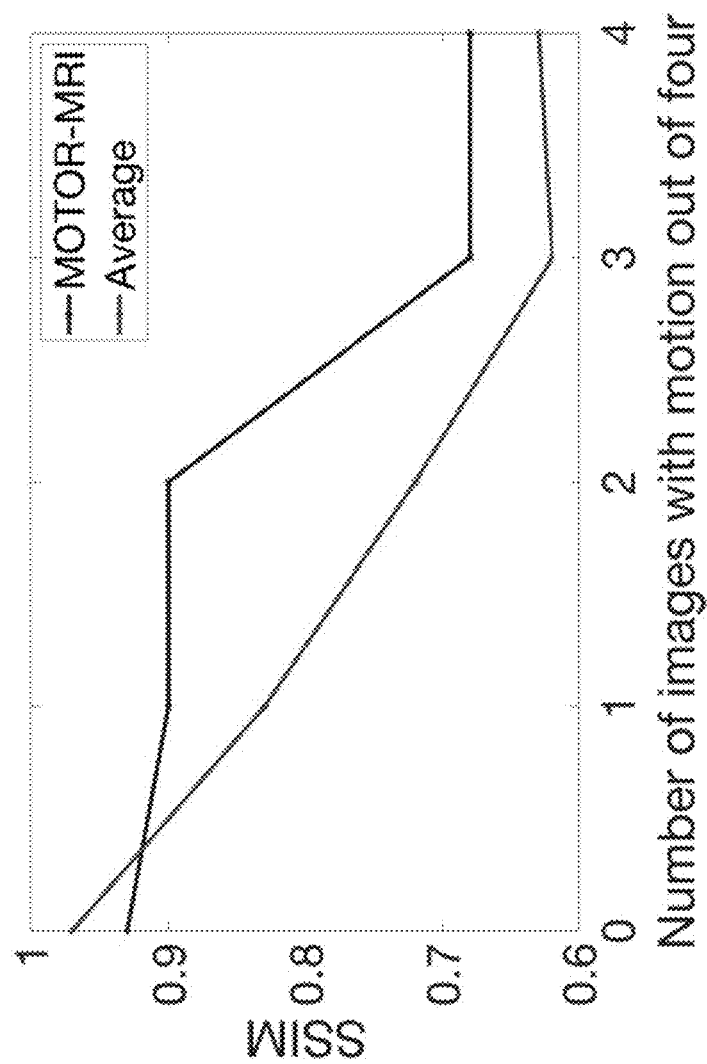
FIG. 11 is a graph showing structural similarity (SSIM) values for MOTOR-MRI and baseline under increasing motion conditions.

Next, we quantify the performance of MOTOR-MRI with respect to increased periods of motion through the cadaver experiment. FIG. 11 quantifies the performance of MOTOR-MRI under increasing motion conditions, by calculating the average structural similarity (SSIM) score between the motion free reference and each of the reconstructions. When no motion is present, the performance of MOTOR-MRI is similar to that of a voxel-wise averaging in terms of the SSIM score. However, when motion is introduced, the SSIM scores for the baseline decrease rapidly, while the SSIM scores for MOTOR-MRI remain high and degrade in a more moderate fashion. When all repetitions are affected by severe motion, no improvement is produced by MOTOR-MRI, as expected. FIG. 11 further shows that MOTOR-MRI can achieve robust performance in the presence of heavy motion conditions, even when most images are affected by motion.

Figure 12:
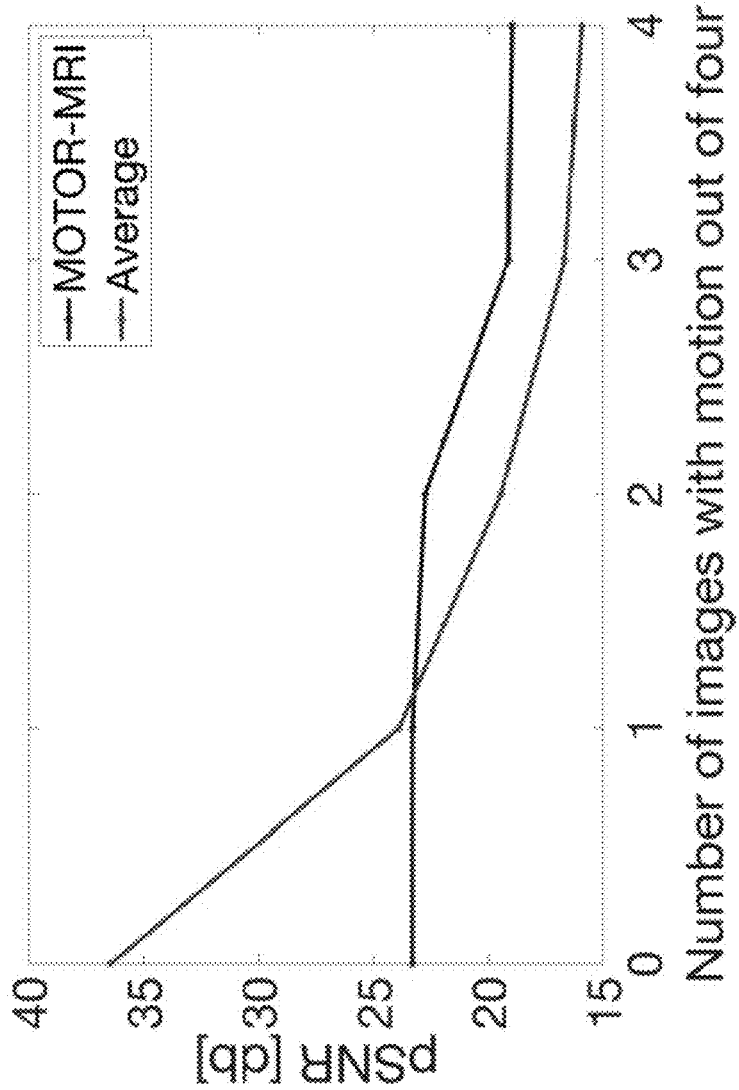
FIG. 12 is a graph showing peak SNR (pSNR) values for MOTOR-MRI and baseline as a function of increasing motion affected repetitions.

This can be further seen by reviewing pSNR values. In FIG. 12, the results of a pSNR analysis are provided for the cadaver experiment. As shown in FIG. 12, two phenomena are clearly visible. First, the pSNR values when there is no motion are higher for the average baseline, compared with the proposed MOTOR-MRI image. Second, when motion is present, MOTOR-MRI consistently achieves higher pSNR scores. The reduction in pSNR for MOTOR-MRI when no movement is present happens due to the Fourier domain weighted average, which achieves higher contrast, but at a cost of some increase in noise. Thus, by adjusting the threshold or the weighting, this can be user or system selected, for example, based on user preference or clinical application.

Figure 13A:
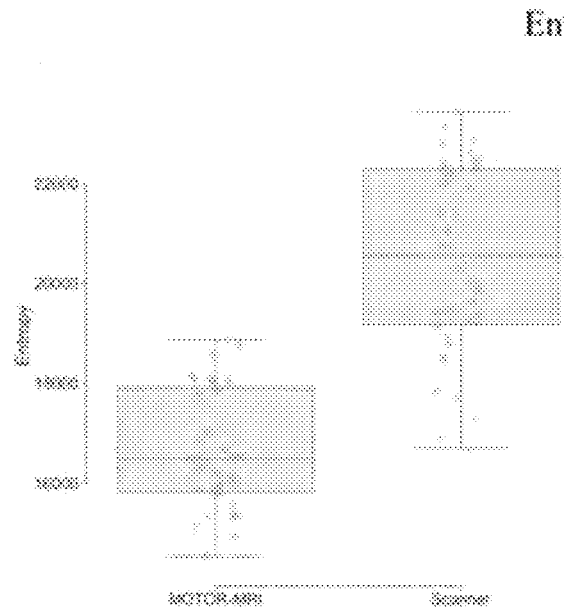
FIG. 13A is a box-plot of entropy scores for MOTOR-MRI and original scanner images for the subjects of Table 2, which lower is better.
Figure 13B:
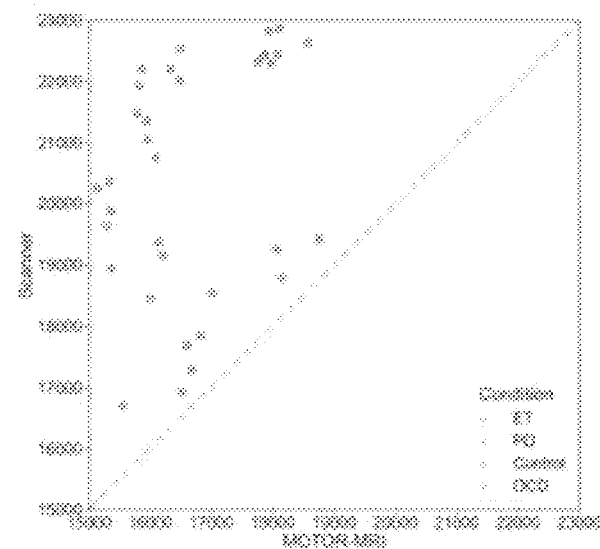
FIG. 13B is a scatter plot of entropy scores between MOTOR-MRI and the original scanner images.
Figure 13C:
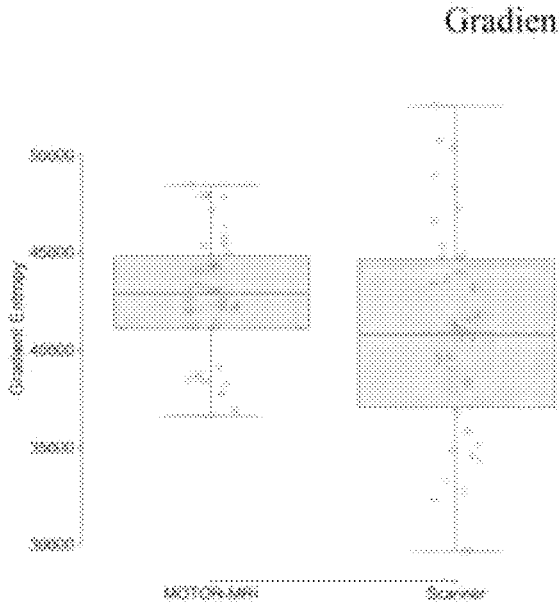
FIG. 13C is a box-plot of gradient entropy scores for MOTOR-MRI and original scanner images for the subjects of Table 2, where higher is better.
Figure 13D:
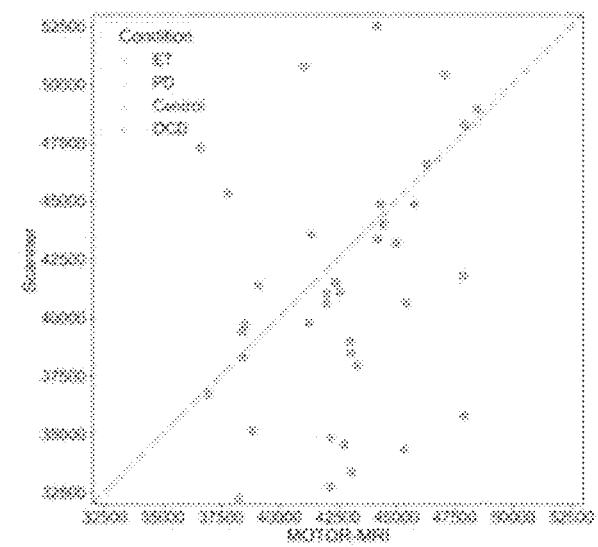
FIG. 13D is a scatter plot of gradient entropy scores between MOTOR-MRI and the original scanner images.

Subjects' demographics are given in Table 4. FIGS. 13A-13D present a quantitative analysis using two accepted metrics in the MR motion mitigation literature. In FIGS. 13A and 13B, the entropy of each of the images is measured (final MOTOR-MRI images as well as the final scanner produced images using all acquired RIS, per subject). In FIGS. 13C and 13D, the gradient entropy of each image, per subject is measured. The entropy of an image, as defined in Atkinson et al. (1997a, b), measures the level of entropy, or disorder in an image's grayscale values. Typically, a motion corrupted image will be associated with a higher level of disorder, due to artifacts, and lower entropy may also be considered as a sign of high contrast (since motion artifacts tend to blend the image grayscale values). Thus, lower values of entropy imply better image quality.

TABLE 4

Subject Demographics

| ID | Gender | Age | Condition | Scanner | # coronal | # axial | # RIS |
|---|---|---|---|---|---|---|---|
| 1 | Male | 54 | Control | 3 T | 2 | 0 | 5 |
| 2 | Male | 35 | Control | 3 T | 1 | 1 | 5 |
| 3 | Male | 54 | Control | 7 T | 6 | 1 | 4 |
| 4 | Female | 69 | Control | 7 T | 0 | 1 | 4 |
| 5 | Female | 27 | Control | 7 T | 6 | 2 | 4/5 |
| 6 | Female | 71 | PD | 7 T | 1 | 0 | 5 |
| 7 | Female | 62 | PD | 7 T | 2 | 2 | 4 |
| 8 | Male | 74 | PD | 7 T | 1 | 1 | 5 |
| 9 | Female | 70 | PD | 7 T | 1 | 0 | 4 |
| 10 | Male | 63 | PD | 7 T | 2 | 2 | 5 |
| 11 | Female | 21 | OCD | 7T | 1 | 1 | 4 |
| 12 | Male | 30 | OCD | 7 T | 1 | 0 | 4 |
| 13 | Female | 63 | ET | 7 T | 1 | 2 | 5 |

FIG. 13A shows a box-plot analysis of the entropy values for each subject, both for the original scanner images and MOTOR-MRI images. MOTOR-MRI achieves statistically significant lower values than the scanner-produced images (p-value<0.05 using a one-way repeated measures analysis of variance (ANOVA)). Panel (B) presents a scatter plot of the same values, scanner values against the corresponding MOTOR-MRI values. Different colors indicate different condition per each subject. Clearly, all values are above the dashed line, indicating that MOTOR-MRI images achieve lower entropy values for each scan, implying sharper and motion-attenuated images.

FIGS. 13C and 13D present a gradient entropy analysis for each image, per subject. Gradient entropy calculates the entropy of the gradients image, and thus higher values indicate images with higher contrast and more visible edges (image blur tends to smooth edges). FIG. 13C presents a box-plot analysis, similar to FIG. 13A, while FIG. 13D shows a scatter plot analysis, similar to panel FIG. 13B. While MOTOR-MRI did not exhibit statistically significant improvement over scanner images (p-value>0.05, one-way repeated measures ANOVA), closer examination of FIG. 13D shows that more gradient entropy scores are higher for the MOTOR-MRI images, than the scanner images.

Figure 14:
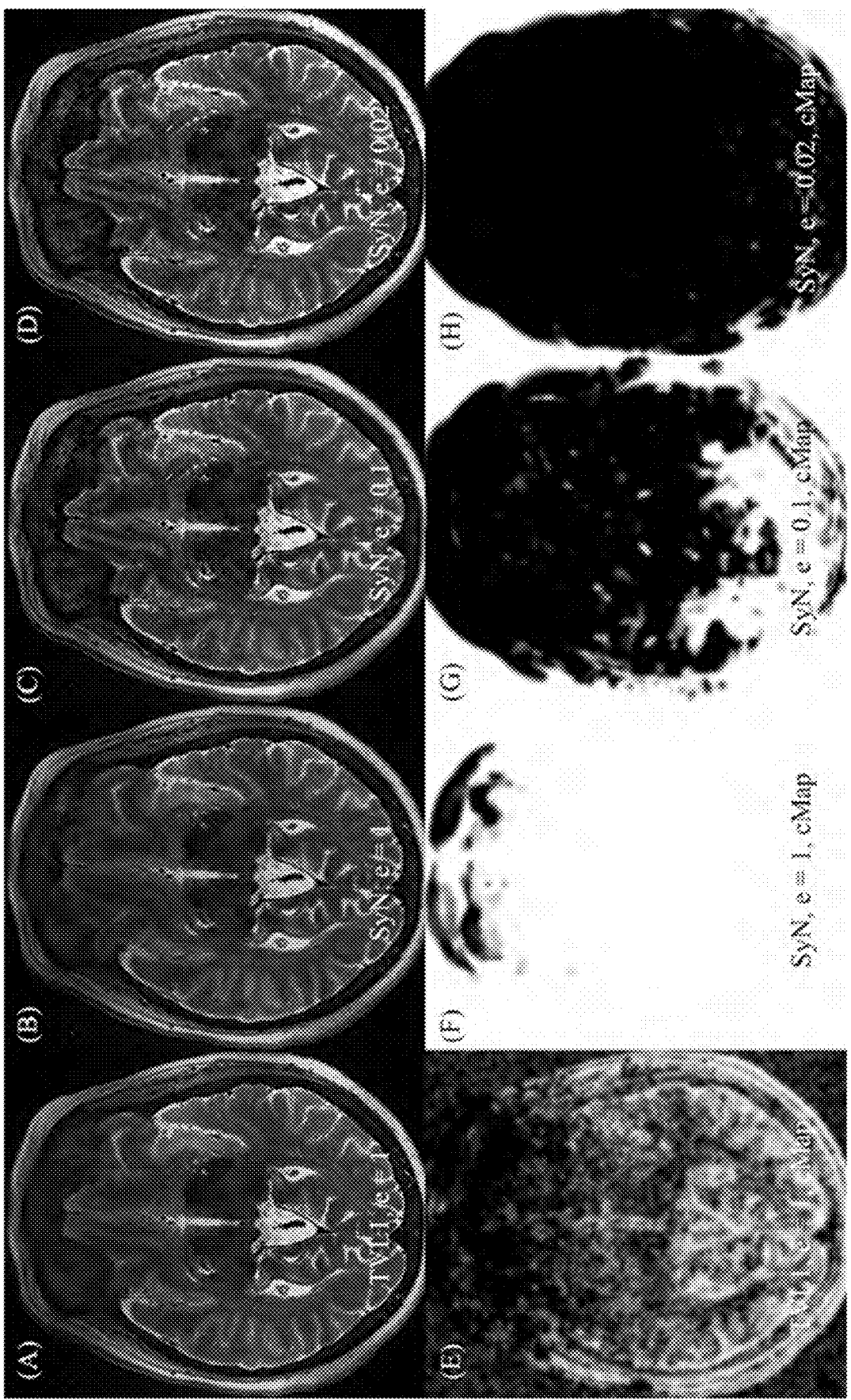
FIG. 14 is a set of correlated images illustrating the impact of registration method on MOTOR-MRI, wherein image (A) shows TVL1-based registration, e=1; images (B)-(D) show SyN based registration, e=1, 0.1, 0.02, respectively; and images (E)-(H) show selected cMaps between a motion free RIS and a motion corrupted RIS for the different images (A)-(D), respectively.

As described above, MOTOR-MRI can operate, in principle, with any non-linear registration method. In FIG. 14, MOTOR-MRI's performance is compared when using either OF-based registration (TVL1), or a more MR-specific registration technique, specifically symmetric normalization (SyN), implemented in the (python implementation of) Advanced Normalization Toolbox (ANTs). Both registrations were carried out with default parameters (i.e. mutual-information cost function for SyN). Image (A) shows an axial MOTOR-MRI image when TVL1-based registration was used (consistency map threshold was set to e=1). This is the same ET patient presented in FIG. 9). Images (B)-(D) depict the corresponding SyN-based MOTOR-MRI images for different values of e (1, 0.1 and 0.02, respectively).

Images (E)-(H) present exemplary cMaps corresponding to each image (A)-(D), respectively.

Observing images (A)-(D), OF-based MOTOR-MRI achieves both a motion-free and smooth image, compared with the SyN based results. When the consistency threshold e is reduced, SyN-based images become noisier. This is mostly evident in the anterior region of images (B)-(D). Images (D) of FIG. 14 shows that OF-based registration blends most regions within the brain apart from the anterior region, where motion is more dominant. Image (F) illustrates that a threshold of e=1 is too high, resulting in a blurred image (B). Reducing the value more trades blur/misregistration with noise (image (C)), until the point in which almost every pixel is dimmed inconsistent (image (H)) and thus the resulting SyN-based image appears motion-free, albeit very noisy (image (D)).

To quantify the level of motion, we performed several controlled experiments, in which we exemplify severe motion. A healthy volunteer was scanned four different times, each scan comprising four RIS. In each scan, motion (3D translations and rotations) was measured via the bore mounted MPT camera. In each subsequent experiment, the volunteer was instructed to lie normally and gradually move for longer periods of time. Relative motion was calculated by subtracting a moving average from each measurement. The moving average was taken over a window of ~6.66 minutes, to account for possible drift which might occur during the scan on one hand, and to still be calculated relative to the average initial position, on the other.

Peak translations often exceeded 10 mm and up to 20 mm and peak rotations range between 4-6 degrees (and at times even 10 degrees). Consequently, severe motion can be quantified as motion which exhibits either translations exceeding 10 mm and rotations higher than 4-6 degrees.

Since MOTOR-MRI is a retrospective motion-mitigation technique, which operates on the already acquired data/images, it can also be used as a complementary technique with other motion-mitigation techniques, and in particular with prospective motion correction (PMC) techniques. In one, a T2-weighted coronal image, comprising 4 RIS, was acquired with the aid of a camera based PMC system from a healthy volunteer. The volunteer was instructed to lie normally during the first half of the experiment (roughly the first two RIS in the sequence) and start moving in the other half, such that a severe motion scenario would be produced. The subject moved significantly, with translations exceeding 5 mm and even 10 mm at times, as well as more than 4 degrees of rotations. It was evident that in this case, PMC could not correct for the severe motion and the image was blurred and suffers from severe ghosting artifacts. When using the same four RIS produced by the scanner with PMC turned on to produce the MOTOR-MRI image (entropy score: 15, 134, gradient entropy score: 44, 207), the difference was distinct. Compared to a motion free image taken from the scanner (4 RIS) in another scan with PMC turned off, as reference, MOTOR-MRI was able to complement the PMC system and improve the image quality, both visually and quantitatively as reported by the entropy and gradient entropy values.

Robust MR imaging in the presence of subject motion has profound clinical applications. In a clinical setting for example, motion artifacts might result in improper detection of tumor borders. In DBS applications, motion artifacts and blur result in improper delineation of sub-cortical nuclei; a region that contains many DBS targets. Moreover, accurate identification of small blood vessels is important for any procedures and surgery pre-planning. As demonstrated above, motion affected images might lead to improper depiction of these fine features.

MOTOR-MRI can effectively mitigate motion artifacts and blur introduced by subject motion.

Through the utilization of the FBA algorithm and a discrimination mechanism, MOTOR-MRI does not rely on explicit modelling of structured motion, which may often be violated (e.g., due to non-rigid movement of body parts—blood vessels pulsation, additional movement of the neck, etc.—and inhomogeneities in the magnetic gradient fields). As such, no explicit model for the image, artifacts, or blurring mechanism is used. That is, the exact mathematical formulations of the blur kernels $k_i$ and motion artifacts $o_i$ are not required for MOTOR-MRI. Instead, MOTOR-MRI can use the aggregation of locally consistent regions between the different RIS in the acquisition process. This is at the essence of MOTOR-MRI's motion robustness, and is especially important in cases where 3D motion modelling may be insufficient, such as in slab acquisitions which capture a limited projection of the full 3D range of motion (e.g., out-of-plane motion: the thinner the slab, the harder it will be to parameterize the 3D motion based on the available data). In fact, MOTOR-MRI's use of deformable registrations, even when the motion is predominantly rigid, is what allows the algorithm to detect local inconsistencies between the individual RIS. This procedure, which generates the consistency maps, allows the technique to detect motion artifacts and propagate only the consistent and sharp parts of the images between them to produce a sharp and clean image. However, a combination of both rigid and non-rigid registrations can also be used in MOTOR-MRI. The application of MOTOR-MRI to both slab acquisitions (e.g., FIG. 7 and FIG. 9) and whole brain scans demonstrates its ability to handle complex, out-of-plane motion successfully.

MOTOR-MRI can work with any type of deformable registration technique. In recent years, MR-specific registration tools have been developed. However, despite their success in the field of medical image registration, these techniques may be considered or adapted for MOTOR-MRI. As mentioned, MOTOR-MRI relies on the process of registration not only to register the different RIS, but also to detect local motion artifacts and inconsistencies between them, and this is a key element in its process. Modern registration techniques calculate a diffeomorphic transformation, and are designed such that the transform be invertible (which implies bijectiveness). That is, if the registration takes a point A to B, then it's inverse should take point B to A. Thus, these types of registration techniques are designed to find a consistent map between each two RIS. However, the OF-based registration technique used in this work is not designed to be invertible. Thus, it can be used as a motion artifact and local inconsistencies detector. This process is exemplified in FIG. 14. SyN-based cMaps are either entirely consistent (image (F) of FIG. 14), which result in a blurred image (B) of FIG. 14, or are extremely inconsistent (image (D) of FIG. 14) when the threshold is reduced dramatically, resulting in a noisy image (D) of FIG. 14. This is in fact an almost total rejection of the other motion affected RIS, thus, in this case MOTOR-MRI cannot perform any blending of information.

Another benefit of MOTOR-MRI is its flexibility. In contrast to other motion correction techniques, MOTOR-MRI operates on the reconstructed images, and not on the acquired k-space data. As such, MOTOR-MRI utilizes computer-vision based tools such as the FBA algorithm and expand it to MR imaging, as well as act as a complementary method to potentially any other motion-correction technique. Since MOTOR-MRI operates on images, it is agnostic to the specific MR acquisition protocol (does not change the acquisition protocol, provided it has access to multiple RIS), and can potentially operate on data acquired with any type of variation to the sampling trajectory (e.g. custom-built trajectories which are more robust to subject movement or navigator-based techniques. As described above, MOTOR-MRI is seamlessly integrated with a camera-based PMC technique and further improves the resulting image quality. It can correct for severe motion that leads to motion artifacts which cannot be corrected solely with the use of the PMC technique. Thus, MOTOR-MRI can complement other techniques to provide further motion robustness. It is worth noting that, in some situations, it may be possible to improve the PMC performance by choosing much tighter rejection bounds. However, this strategy may increase scan duration and would typically require parameter tuning to find suitable rejection thresholds which can generalize to many scenarios. In practice, this may be a limiting factor, especially when scanning patients. MOTOR-MRI complements PMC by directly operating on its reconstructed images, without the need for extensive (and perhaps even patient-specific) parameter tuning.

As demonstrated in FIG. 9, MOTOR-MRI can correct for motion artifacts in real-life scenarios, where patients with motor dysfunctions are scanned. As noted, requirements such as the use of wearable markers for PMC, is often impractical. However, MOTOR-MRI is suitable for different scanner types and field strengths (e.g., 3 T and 7 T) as well as to clinical acquisition protocols.

As described above, the performance of MOTOR-MRI has been quantified under varying acquisition conditions, scanners, and neurological disorders. FIGS. 13A-13D illustrate the performance of MOTOR-MRI based performance on accepted metrics in the motion-correction literature, image entropy (FIGS. 13A and 13B) and image gradient-entropy (FIGS. 13C and 13D), for healthy control subjects as well as patients with neurological disorders. For example, FIGS. 13A and 13B clearly show that all MOTOR-MRI images achieve statistically significant lower entropy scores compared with the equivalent scanner outputs. This quantitative analysis, as well as the qualitative demonstrations, provide clear insights to the benefits of MOTOR-MRI and its potential.

We note that MOTOR-MRI utilizes multiple RIS of the same imaged volume to operate. While this might seem limiting, some sequences already rely on repetitive acquisitions to improve SNR. MOTOR-MRI operates on the same acquired data to produce equivalent yet motion-robust images. In fact, since MOTOR-MRI operates directly on the acquired images, it can work in conjunction with any type of k-space acceleration techniques, such as GRAPPA, compressed sensing MRI, and/or deep-learning based techniques. In practice, we have shown both quantitatively and qualitatively that adequate images are produced with 4 to 5 image RIS. With the advancement in faster k-space acquisitions, total acquisition time is expected to be further reduced. This may allow for increased number of RIS without compromising current clinical maximum acceptable scan time while allowing for additional improvement in image quality and motion robustness using the proposed MOTOR-MRI post-processing approach.

In this work, each of the RIS was acquired with a 3-fold GRAPPA acceleration factor. With this acceleration factor no noticeable reconstruction artifacts were observed. Since multiple coils are used, each individual scan suffers increased noise and g-factor, compared with an equivalent non-GRAPPA image. However, an equivalent non-GRAPPA image would be highly susceptible to patient motion (without any additional aid). By breaking the total acquisition into several (accelerated) RIS, MOTOR-MRI can provide robustness against patient motion. Although each individual RIS suffers from increased noise, the weighted averaging operation boosts the SNR lost due to the GRAPPA acceleration.

The acquisition protocol used in this work has the same total acquisition time as a scan with a 33-66% larger FOV and no GRAPPA acceleration. Although this implies oversampling of k-space, each scan was acquired with 4-5 RIS, as the total scan duration was still within clinically acceptable scan times. In fact, MOTOR-MRI was demonstrated and tested for 2D T2-weighted 2D TSE sequences. By further accelerating the acquisition, multiple RIS of time-consuming sequences (e.g., 3D acquisitions) can be acquired within clinically acceptable scan times, while achieving motion robustness.

As mentioned before, MOTOR-MRI can be used directly on the reconstructed images without any additional processing or be added as a complementary process to motion-correction techniques which utilize such acceleration. The averaging and discrimination mechanism of MOTOR-MRI can be thought of as providing a trade-off between artifact mitigation and SNR. Equations (8) and (9) provide means to propagate only consistent information between the different RIS and to exclude, or at least heavily mitigate, motion artifacts. In the first iteration and based on the calculated entropy of the consistency maps, the algorithm may need to decide to rely on eqns. (8) or (9) to perform the image blending. Two scenarios are worth noting. First, as can be seen in FIG. 5, when one image is relatively motion free (image (A)) and the other is motion corrupted (image (C)), the resulting consistency map (image (E)) will be sparse. This in turn will result in the averaging algorithm rejecting locally corrupted regions from the motion corrupted image, but keeping consistent information from motion free regions (such as the ventricles region in image (C)).

Notably, when both images are considered heavily corrupted by motion, no blended image is produced. Thus, in effect, Fourier domain aggregation is performed with fewer images, which reduces the SNR (locally). In practice, total rejection of locally motion corrupted images is rare (unless an image is completely motion corrupted), and in most cases these regions will be assigned very low weights in their respective consistency maps (i.e. image (E) of FIG. 5).

MOTOR-MRI expects that at least one RIS will be relatively motion free. In practice, this condition is met when at least one of the RIS is not severely affected by motion. This RIS does not need to be motionless or extremely sharp, just clearer than the images which are heavily corrupted by motion. In our experience when scanning patients with motor dysfunctions, involuntary movement does not always occur throughout all the scan duration but rather in shorter episodes, such that in practice the above condition is often met. In practice, MOTOR-MRI can provide clear and sharp images even when imaging PD and ET patients, as was demonstrated.

MOTOR-MRI was run on a system with 2 Intel Xeon silver 4125 processors operating at 2.5 GHZ (total of 32 threads) and 250 GB RAM. One implementation was written purely in python and supports multi-processing. Runtime for a single iteration using OF-based registration when four RIS were acquired was about 14 minutes and 16-17 minutes when five RIS were acquired with the resolutions provided above.

In this work we presented a method for motion robust MRI for anatomical scans. The technique can salvage motion corrupted images, which otherwise may not be usable. MOTOR-MRI does not prolong the scan time or changes the acquisition protocol if it already includes multiple RIS and does not require any explicit modelling of the motion degradation mechanism. Instead, it relies on the propagation of locally sharp content between multiple acquisitions to achieve a sharp and clear image. MOTOR-MRI is applicable to different types of MR scanners (e.g., manufacturer, 3 T or 7 T, clinical or research imaging protocols), can be used independently or in conjunction with other motion correction techniques (e.g., prospective correction) and can operate in different scan orientations (e.g., coronal and axial). Although demonstrated on T2-weighted TSE brain scans, future prospects include its ex-tension to other MR modalities, as well as additional organs.

As noted before, MOTOR-MRI has several key aspects that distinguish it from traditional motion correction techniques. First, MOTOR-MRI is a retrospective method. Most prospective motion correction techniques, such as navigators, actively modify the acquisition protocol during scan to account for patient movement and might prolong the scan time. In contrast, MOTOR-MRI does not change the acquisition protocol or total scan time, and does not require on any external hardware, such as motion tracking cameras, but can be used with such hardware nevertheless. MOTOR-MRI operates directly on images acquired with standard clinical protocols. MOTOR-MRI is suitable to any acquisition protocol that uses or can be modified to use multiple repetitions. Moreover, prospective navigation techniques always assume a parameterized model for patient motion. This assumption can be violated, such as due to non-rigid movement of body parts and inhomogeneities in the magnetic gradient fields. MOTOR-MRI does not rely on a specific motion or image model, or a specific model for the artifacts and image blur. That is, the exact mathematical formulations of the blur kernels $k_i$ and motion artifacts $o_i$ are not required for MOTOR-MRI. Instead, MOTOR-MRI uses the aggregation of locally consistent regions between the different repetitions in the acquisition process. This adds another dimension of robustness to MOTOR-MRI. In fact, MOTOR-MRI's utilization of deformable registrations, even when the motion is predominantly rigid, is what allows the algorithm to detect local inconsistencies between the individual repetitions. This procedure, which generates the consistency maps, allows the technique to detect motion artifacts and propagate only the consistent and sharp parts of the images between them to produce a sharp and clean image. Although we have used optical flow-based registrations to calculate the displacement field of each image, other deformable registration techniques can be used, such as described in the following, which are incorporated herein by reference in their entirety: B. B. Avants, C. L. Epstein, M. Grossman, and J. C. Gee, \Symmetric diffeomorphic image registration with cross-correlation: evaluating automated labeling of elderly and neurodegenerative brain," Medical image analysis, vol. 12, no. 1, pp. 26-41, 2008; J. Ashburner, \A fast diffeomorphic image registration algorithm," Neuroimage, vol. 38, no. 1, pp. 95-113, 2007; and T. C. Mok and A. C. Chung, \ Large deformation diffeomorphic image registration with Laplacian pyramid networks," in International Conference on Medical Image Computing and Computer-Assisted Intervention. Springer, 2020, pp. 211-221.

Deep-learning (DL) based techniques are also (currently) retrospective and operate on acquired images. Although these techniques show promising results, their clinical application may be limited. These networks are trained in a fully supervised manner, based on simulated motion, which in turn induces simulated motion artifacts. Although visually similar to artifacts achieved in real acquisitions, training on purely simulated data may not entirely capture all possible types of motion corruption (e.g., parts of non-rigid motion). For example, the images presented in FIG. 9 show typical ringing artifacts which are associated with patient movement, but also noticeable image blur. A network trained to remove these artifacts may not necessarily sharpen the image correctly. Currently, to widen their applicability, deep architectures require additional training when new modalities, scanning fields (i.e., 3 T or 7 T), or anatomical structures are introduced.

We note that MOTOR-MRI uses multiple repetitions of the same imaged volume. Although this may sound limiting at first, clinical sequences such as the T2-weighted 2D TSE already rely on repetitive acquisitions to improve SNR. MOTOR-MRI operates on the same acquired data to produce equivalent motion robust images. In fact, since MOTOR-MRI operates directly on the acquired images, it can work in conjunction with any type of k-space acceleration techniques, such as generalized autocalibrating partially parallel acquisitions (GRAPPA), compressed sensing MRI, and recently-introduced deep-learning based techniques. In practice, we have shown that excellent images are produced with 4 to 5 image repetitions. This number of repetitions is similar to the number of repetitions used in standard clinical protocols. With the advancement in faster k-space acquisitions, total acquisition time is expected to be further reduced. This, in turn may allow for increased number of image repetitions without compromising current clinical maximum acceptable scan time while allowing improvement in image quality using the here proposed MOTOR-MRI post-processing approach.

MOTOR-MRI can be thought of as providing a trade-off between artifact mitigation and SNR. Equations (8) and (9) provide means to propagate only consistent information between the different repetitions and to exclude, or at least heavily mitigate, motion artifacts. In the first iteration and based on the calculated entropy of the consistency maps, the algorithm may need to decide to rely on equation (8) or equation (9) to perform the image blending. In this case, when both images are considered as heavily corrupted by motion, no blended image is produced. Thus, in effect, Fourier domain aggregation is performed with fewer images, which reduces the SNR (locally). We note, however, that even the motion corrupted images are not typically being discarded altogether. Motion-corrupted images can and are still being blended together with sharp images, as described by Table 1. We note that although in this work the algorithm selects whether to use equation (8) or equation (9), in principle, this decision can be made continuous, such that the resulting blended image is a linear combination of both equations.

As was shown in FIG. 11, when all repetitions are heavily motion corrupted, MOTOR-MRI does not have any repetitions with locally sharp information to propagate. Since MOTOR-MRI blends image information locally to yield the desired results, MOTOR-MRI performs best with relatively sharp and motion free local information present between the individual repetitions, at least once. In practice, this condition is met when at least one of the repetitions is not severely affected by motion (order does not matter). This repetition does not need to be motionless or extremely sharp, just clearer than the images which are heavily corrupted by motion. In experiments, when scanning PD patients, involuntary movement does not always occur throughout all the scan duration but rather in shorter episodes, such that in practice the above condition is often met.

Thus, MOTOR-MRI can salvage motion corrupted images, which otherwise may not be usable. MOTOR-MRI does not change the acquisition protocol if it already includes multiple repetitions, does not require any specific knowledge of the motion degradation mechanism, and does not rely on learned priors which may introduce incorrect grayscale values. Instead, it uses the propagation of locally sharp content between multiple acquisitions to achieve a sharp and clear image. MOTOR-MRI is applicable to any type of MR scanner (e.g., 3 T and 7 T, clinical or research imaging protocols), and although demonstrated on T2-weighted images, MOTOR-MRI is applicable in principle to any MR modality and orientation (i.e., axial, coronal and sagittal), provided it has access to multiple repetitive scans.

As used in the claims, the phrase "at least one of A, B, and C" means at least one of A, at least one of B, and/or at least one of C, or any one of A, B, or C or combination of A, B, or C. A, B, and C are elements of a list, and A, B, and C may be anything contained in the Specification.

The present invention has been described in terms of one or more preferred embodiments, and it should be appreciated that many equivalents, alternatives, variations, and modifications, aside from those expressly stated, are possible and within the scope of the invention.

The invention claimed is:

1. A method including steps comprising:
   (a) accessing a plurality of candidate images reconstructed from magnetic resonance (MR) data acquired with multiple repetitions of region of interest (ROI) in a subject, wherein at least a portion of the plurality of candidate images includes motion artifacts;
   (b) selecting a candidate image of the ROI in the subject;
   (c) registering the candidate image to a reference image;
   (d) comparing the candidate image to a consistency map;
   (e) based on comparing the candidate image using the consistency map, selecting a blending algorithm;
   (f) generating a blended image using the blending algorithm and the candidate image;
   (g) repeating steps (b)-(f) for each candidate image;
   (h) performing a Fourier aggregation to generate a combined image; and
   (i) displaying the combined image with reduced motion artifacts compared to the plurality of candidate images.

2. The method of claim 1 wherein step (e) includes selecting between a first blending algorithm that weights toward the candidate image and a second blending algorithm that weights toward the reference image.

3. The method of claim 1 wherein the blended image is formed using at least two of the candidate images, the reference image, and the candidate map.

4. The method of claim 1 wherein the combined image is formed by propagating only consistent information between the different repetitions of data acquisitions into each candidate image.

5. The method of claim 1 wherein step (a) includes acquiring the candidate images from one of a server having the images stored therein from a prior acquisition of the MR data and reconstruction of the candidate images or an MR imaging (MRI) system.

6. The method of claim 1 wherein each of the candidate images correspond to a respective repeated individual scan (RIS).

7. The method of claim 1 further comprising receiving a user selection of a preference for blending of signal-to-noise ratio, or motion robustness.

8. The method of claim 1 wherein the Fourier aggregation is a voxel-wise weighted average in a Fourier domain.

9. The method of claim 1 wherein the consistency map provides a threshold for selecting the blending algorithm.

10. The method of claim 1 further comprising performing one of an entropy calculation between a given candidate image and the consistency map, or calculating a structural similarity index (SSIM) between a given candidate image and the consistency map to select the blending algorithm.

11. The method of claim 1 wherein the candidate image is a transformed or filtered image.

12. A magnetic resonance imaging (MRI) system comprising:
   a magnet system configured to generate a polarizing magnetic field about at least a portion of a subject arranged in the MRI system;
   a plurality of gradient coils configured to apply magnetic gradients to the polarizing magnetic field;
   a radio frequency (RF) system configured to apply an excitation field to the subject and acquire MR image data from the subject;
   a computer system programmed to carry out steps comprising:
      (a) controlling the plurality of gradient coils and the RF system to acquire MR data as multiple repetitions of region of interest (ROI) in the subject;
      (b) reconstructing a plurality of candidate images from the MR data, wherein at least a portion of the plurality of candidate images includes motion artifacts;
      (c) selecting a candidate image of the ROI in the subject;
      (d) registering the candidate image to a reference image;
      (e) analyzing the candidate image using a consistency map;
      (f) based on analyzing the candidate image using the consistency map, selecting a blending algorithm;
      (g) generating a blended image using the blending algorithm and the candidate image;
      (h) repeating steps (c)-(g) for each candidate image reconstructed from the MR image data in step (b);
      (i) performing a Fourier aggregation to generate a combined image; and
   a display to display the combined image with reduced motion artifacts compared to the plurality of candidate images.

13. The system of claim 12 wherein step (f) includes selecting between a first blending algorithm that weights toward the candidate image and a second blending algorithm that weights toward the reference image.

14. The system of claim 12 wherein the blended image is formed using at least two of the candidate images, the reference image, and the candidate map.

15. The system of claim 12 wherein the combined image is formed by propagating only consistent information between the different repetitions of data acquisitions into each candidate image.

16. The system of claim 12 wherein each of the candidate images correspond to a respective repeated individual scan (RIS) performed with the MRI system.

17. The system of claim 12 further comprising receiving a user selection of a preference for blending of signal-to-noise ratio, or motion robustness.

18. The system of claim 12 wherein the Fourier aggregation is a voxel-wise weighted average in a Fourier domain.

19. The system of claim 12 wherein the consistency map provides a threshold for selecting the blending algorithm.

20. The system of claim 12 further comprising performing one of an entropy calculation between a given candidate image and the consistency map, or calculating a structural similarity index (SSIM) between a given candidate image and the consistency map to select the blending algorithm.

21. The system of claim 12 further comprising assessing an intrinsic, calculable property of the consistency map to provide a threshold for selecting the blending algorithm.

* * * * *

UNITED STATES PATENT AND TRADEMARK OFFICE
CERTIFICATE OF CORRECTION

PATENT NO. : 12,174,281 B2
APPLICATION NO. : 17/947761
DATED : December 24, 2024
INVENTOR(S) : Oren Solomon et al.

Page 1 of 1

It is certified that error appears in the above-identified patent and that said Letters Patent is hereby corrected as shown below:

In the Specification

Column 12, Line 16, "&" should be --$\xi$--.

Column 22, Line 61, "GHZ" should be --GHz--.

Signed and Sealed this
Fourth Day of March, 2025

Coke Morgan Stewart
*Acting Director of the United States Patent and Trademark Office*